US012059581B2

(12) United States Patent
Bottura

(10) Patent No.: US 12,059,581 B2
(45) Date of Patent: Aug. 13, 2024

(54) GANTRY AND APPARATUS FOR FOCUSSING BEAMS OF CHARGED PARTICLES

(71) Applicant: CERN—European Organization For Nuclear Research, Geneva (CH)

(72) Inventor: Luca Bottura, Commugny (CH)

(73) Assignee: CERN—European Organization For Nuclear Research, Geneva (CH)

( * ) Notice: Subject to any disclaimer, the term of this patent is extended or adjusted under 35 U.S.C. 154(b) by 934 days.

(21) Appl. No.: 17/056,234

(22) PCT Filed: May 21, 2019

(86) PCT No.: PCT/EP2019/063152
§ 371 (c)(1),
(2) Date: Nov. 17, 2020

(87) PCT Pub. No.: WO2019/224215
PCT Pub. Date: Nov. 28, 2019

(65) Prior Publication Data
US 2021/0187328 A1    Jun. 24, 2021

(30) Foreign Application Priority Data

May 21, 2018    (EP) .................................... 18173426

(51) Int. Cl.
*A61N 5/10* (2006.01)
*G21K 1/093* (2006.01)
*G21K 5/04* (2006.01)

(52) U.S. Cl.
CPC ........... *A61N 5/1081* (2013.01); *G21K 1/093* (2013.01); *G21K 5/04* (2013.01); *A61N 2005/1087* (2013.01)

(58) Field of Classification Search
CPC ...................................................... G21K 1/093
See application file for complete search history.

(56) References Cited

U.S. PATENT DOCUMENTS

2016/0247591 A1    8/2016    Bromberg et al.

FOREIGN PATENT DOCUMENTS

| JP | H07227435 A | 8/1995 |
| WO | 2010098894 A1 | 9/2010 |

OTHER PUBLICATIONS

PCT Patent Application No. PCT/EP2019/063152 International Search Report and Written Opinion dated Aug. 5, 2019.
European Patent Application No. 18173426.0 Search Report dated Dec. 7, 2018.
Indian Patent Application 202047050114 Examination Report dated Apr. 22, 2022.

*Primary Examiner* — Thaddeus B Cox
(74) *Attorney, Agent, or Firm* — Erise IP, P.A.

(57) ABSTRACT

A gantry is provided for focusing beams of charged particles having differing momentum to charge ratios to a substantially common point. The gantry comprises at least one toroidal magnet having a central bore and a primary axis extending along the central bore and configured to receive beams of charged particles at different radial locations dependent on the momentum to charge ratio of the beam. The toroidal magnet comprises a plurality of discrete, substantially planar coils spaced apart and extending radially from the primary axis and configured to produce a magnetic field that is periodically symmetric about the primary axis.

21 Claims, 14 Drawing Sheets

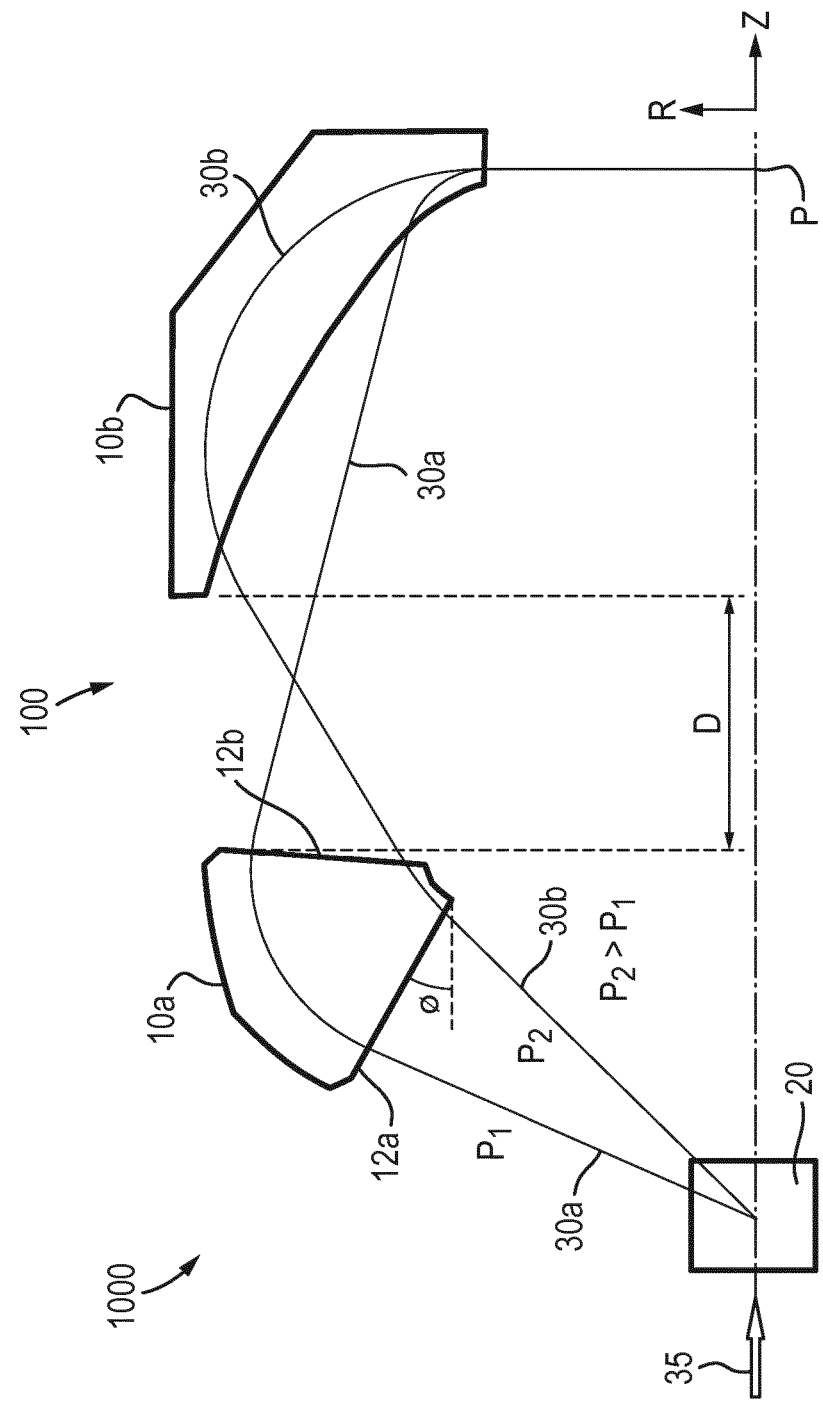

GANTRY AND APPARATUS FOR FOCUSSING BEAMS OF CHARGED PARTICLES

RELATED APPLICATIONS

The present application is a national stage application under 35 U.S.C. § 371 of International Application No. PCT/EP2019/063152, filed 21 May 2019, which claims priority to European Patent Application No. 18173426.0, filed 21 May 2018. The above referenced applications are hereby incorporated by reference in their entirety.

BACKGROUND TO THE INVENTION

It is known to use magnets to deflect, or "bend" charged particles in order to separate particles having different momentum to charge ratios. For example, mass spectrometers and particle detectors work on the principle that particles having different momentum to charge ratios will deflect by different amounts in the presence of a magnetic field, allowing for analysis of the particles.

Another example of the use of magnetic fields for deflecting charged particles is charged particle therapy, which is a type of radiation therapy. Radiation therapy in general refers to the use of ionizing radiation to treat cancer by killing or controlling malignant tissue. The ionizing radiation damages the DNA of the tissue, which leads to cell death. Conventional radiation therapy uses high energy photons (X-rays) produced from accelerated electrons that are directed to the desired area of the body. In order to minimise damage to healthy tissue, the X-rays are typically introduced at a number of angles, with the beams intersecting at the cancerous area.

When the irradiating beams are comprised of charged particles, radiation therapy is called charged particle therapy. The advantages of charged particle therapy lie in the unique physical and radiobiological properties of these particles; they can penetrate the tissues with little diffusion and deposit the maximum energy just before stopping. This allows a precise definition of the specific region to be irradiated. Such charged particles may include hadrons (e.g. protons, ions such as carbon ions, mesons) and leptons (e.g. electrons).

The beam delivery system is one of the key elements of a charged particle therapy system, whether based on protons, ion beams or other charged particles. In many cases the beam delivery system is a relatively simple and fixed-geometry transfer line. This has limitations on the degree of stereotaxy that can be achieved, as well as unwanted parasitic dose to healthy tissues. This issue has been resolved in a number of installations with a "gantry": a set of magnets that receives the beam extracted at variable energy from a particle accelerator, and directs it onto the patient from an arbitrary direction, possibly with no variation in the centre of delivery irrespective of the beam direction ("iso-centric"), and with no need to move the patient during treatment. A key advantage of a gantry is the ability to "paint" the irradiated region with improved flexibility, accuracy and, ultimately, much reduced parasitic dose.

The beam optics of present gantries are typically based on bending magnets mounted on a rotating structure that bends the beam from the extraction line, straightens it, and finally bends it at 90 degrees with respect to the patient, so that the delivered beam travels a minimum path in healthy tissue. Quadrupoles, steerers and corrector magnets are customarily placed along the transfer line to control the beam transmission.

The desirable beam rigidity of proton beams is in the range of 1.2 to 2.4 Tm (for proton energies in the range of 70 to 250 MeV), while for a typical ion such as carbon the desirable beam rigidity is 3.3 to 6.6 Tm (for nucleon energies in the range of 120 to 430 MeV/u). State-of-the-art gantries based on normal conducting electro-magnets have dipole field strength in the range of 1 to 2 T, and the above rigidities correspond to electro-magnets of several metres length.

The established technology requires that these magnets rotate around the patient, resulting in extremely large structures of high mechanical rigidity, especially for carbon ion therapy. In addition, the field produced by the gantry magnets needs to be variable to some degree, as the magnet bore size alone does not allow accepting the desired energy range. In the established technology the gantry and its rotating mechanical structure represent a very significant burden in terms of weight, footprint and cost, in terms of both initial investment and operation.

Superconducting magnets have been used in order to reduce the size of such gantries. However, the rotating nature of the gantry requires that the accompanying cryogenic system has rotating parts, either based on flexible transfer lines, or cryogenic machineries such as cryo-coolers rotating with the gantry magnets. This adds to the complexity of the design and is undesirable.

SUMMARY OF THE INVENTION

In accordance with a first aspect of the invention there is provided a gantry for focusing beams of charged particles having differing momentum to charge ratios to a substantially common point, comprising: at least one toroidal magnet having a central bore, a primary axis of the toroidal magnet extending along the central bore, the toroidal magnet configured to receive beams of charged particles at different radial locations dependent on the momentum to charge ratio of the beam; wherein the toroidal magnet comprises a plurality of discrete, substantially planar coils spaced apart and extending radially from the primary axis and configured to produce a magnetic field such that, in use, a first beam of charged particles having a component of motion along the primary axis and entering the toroidal magnet at a first radial location, is directed towards a first point on the primary axis, and; a second beam of charged particles having a different momentum to charge ratio to the first beam, and having a component of motion along the primary axis and entering the toroidal magnet at a second radial location, is directed towards said first point on the primary axis, and wherein; the planar coils are configured to produce a magnetic field that is periodically symmetric about the primary axis, and; the at least one toroidal magnet is substantially stationary in use.

The inventor has realised, rather counterintuitively to conventional uses of toroidal magnets, that such a toroidal magnet configuration may be used to focus beams of charged particles having differing momentum to charge (p/q) ratios to the same point along the primary axis of the magnet. This goes against the conventional use of such toroidal magnets that are used to separate the trajectories of particles having different p/q ratios.

The toroidal magnet is configured to receive beams of charged particles at different radial locations dependent on the momentum to charge ratio of the beam. The beams enter a first end of the magnet (where the magnet extends between first and second ends positioned along the primary axis) in the space between adjacent coils. Due to differing radial entry positions, beams of charged particles having different momentum to charge ratios travel different distances within the magnetic field, and are therefore deflected by the magnetic field to a common point on the primary axis. Typically, the toroidal magnet is configured to receive beams of higher momentum to charge ratio (higher energy) at a more radially outward location as compared to beams of lower momentum to charge ratio (lower energy), such that the higher energy beams travel a further distance within the magnetic field and the beams may be deflected to a common point on the primary axis. The toroidal magnet advantageously has a large acceptance.

As will be appreciated by the skilled person, each particle within a beam of particular energy has substantially the same momentum to charge ratio, and thus such a beam may be seen to have a particular momentum to charge ratio. This is particularly the case for beams originating from particle accelerators.

The beams are preferably provided to the toroidal magnet by a bending device (such as a vector magnet, bending crystal or plasma) positioned on the primary axis and configured to direct the beams towards the toroidal magnet at an angle such that the beams enter the magnet at the desired radial location. Thus, the beams typically enter the magnet at an angle to the primary axis, although in other configurations may enter the magnet substantially parallel to the primary axis.

Preferably, in use, beams of charged particles are received at the toroidal magnet at a non-zero angle with respect to the primary axis.

Particularly advantageously, the gantry of the invention is stationary in use, removing the requirement for massive structures and high-precision mechanisms that are used in state-of-the art rotating gantries for beam irradiation. This significantly reduces the footprint, mass and operational complexity of the gantry.

The at least one toroidal magnet being substantially stationary in use allows the gantry to be substantially stationary in use.

The gantry of the present invention finds particularly advantageous application in charged particle therapy. In such an application, in use, a subject (which could be a human or animal) is positioned within the central bore of the at least one toroidal magnet, with the magnetic field produced by the toroidal magnet able to deflect beams of different p/q and entering the magnet at different radial locations to the desired focal point at the location of the subject. The magnetic field is preferably configured such that beams of different p/q are directed to the same point on the primary axis in substantially the same direction (for example at 90 degrees to the primary axis). Advantageously, neither the gantry nor the subject need to be moved, in contrast to state-of-the-art rotating gantries.

In other words, preferably the magnetic field produced by the plurality of discrete, substantially planar coils is further configured such that beams of different momentum to charge ratio are directed towards a substantially common point on the primary axis along a trajectory that is substantially 90 degrees to the primary axis. In embodiments where more than one toroidal magnet is used, the trajectory of the particle beams is substantially 90 degrees to the primary axis preferably after passing through the most downstream toroidal magnet (i.e. the final toroidal magnet that the beams pass through).

The term "charged particle therapy" is used here to mean radiation therapy using irradiating beams of charged particles. Such charged particles may include hadrons (e.g. protons, ions such as carbon ions, mesons) and leptons (e.g. electrons).

The magnetic field produced by the toroidal magnet is periodically symmetric about the primary axis. This may be referred to as toroidally periodically symmetric. This characteristic may be realised by the plurality of planar coils being positioned in a periodic manner about the primary axis. For example, in a preferred configuration, the coils are equally spaced apart in a toroidal direction. In other configurations the coils may not be equally spaced in the toroidal direction, with pairs or groups of coils close to each other, separated by a gap from one pair or group of coils to the next, and overall periodically positioned in the toroidal direction in order to provide the toroidally periodically symmetric magnetic field. For example, in embodiments, the planar coils may be placed in groups of two or more, whereby the groups repeat with toroidal periodicity. The magnetic field produced by the toroidal magnet being periodically symmetric allows beams of charged particles entering the magnet at different locations (both radially and toroidally) and having different p/q ratios to be focused to a common point on the primary axis without the requirement for a rotating gantry.

Preferably, the magnetic field produced by the toroidal magnet is substantially static in use, for example during irradiation of a subject. (Although typically the magnetic field may be changed if required.) The static nature of the toroidal magnet itself and the magnetic field advantageously means that superconducting materials are particularly suitable for the substantially planar coils. Indeed, preferably the plurality of planar coils are superconducting coils. The superconducting coils may be comprised of low temperature superconducting material such as Nb—Ti and $Nb_3Sn$ or high temperature superconducting material such as Rare Earth based (REBCO) or Bismuth based (BISCCO) copper oxides. Advantageously, as the at least one toroidal magnet is stationary in use, cryogenic apparatus for low temperature superconductors is easily installed. In the case of high temperature superconducting materials, simplified, or no such cryogenic apparatus would be required.

The use of superconducting materials for the coils advantageously means that much larger magnetic fields can be used in comparison to normal-conducting solutions, which in turn leads to a significant reduction in size of the gantry. Typical magnetic field strengths used in the present invention may range from 1 T to 10 T, preferably between 2 T and 8 T. The length of the gantry along a direction substantially parallel to the main axis is in the range of 1 m to 5 m. The outer radius of the gantry is typically in the range of 1 m to 3 m, preferably 1.6 m, with the inner radius of the gantry (i.e. the radius of the central bore) typically being in the range of 0.4 m to 1 m, preferably 0.6 m. Typical masses for the gantry may be in the range of 5-20 tonnes for proton beams to 10-30 tonnes for ion (e.g. carbon ion) beams. This represents a substantial weight reduction compared to conventional gantries which may be well over 100 tonnes.

Herein the terms "primary axis" and "main axis" are used interchangeably.

The plurality of coils are each substantially planar. Here the term "planar" is used to mean that the dimension of each coil in a toroidal direction is significantly smaller than its dimensions in the radial and longitudinal (i.e. parallel with the primary axis) directions. The planar nature of the coils means that the space between adjacent coils is relatively large, increasing the ease with which beams of charged particles may enter the toroidal magnet.

In a preferred embodiment, the toroidal magnet comprises 16 coils equally spaced in a toroidal direction. Other numbers and arrangements of coils are envisaged, however, such that the magnetic field exhibits periodic symmetry about the primary axis.

Typically, the planar coils have a non-symmetrical geometry. Here, the coils have a non-symmetrical geometry when viewed in the toroidal direction. Typically the coils are non-symmetric about an axis substantially parallel with the primary axis. Such non-symmetrical geometry aids in producing a magnetic field such that particles with different p/q ratios may enter the toroidal magnet at different radial points and travel different distances through the magnetic field, resulting in a common focus point on the primary axis.

Preferably, the planar coils are elongate in a direction substantially parallel to the main axis, and have a geometry such that a radial dimension of the coils varies along the elongate length. In preferred embodiments, each planar coil has a minimum radial dimension at a first end of the toroidal magnet and a maximum radial dimension at a second opposing end of the toroidal magnet. Typically, the minimum radial dimension is at the end where the beam of charged particles enters the magnet, with the maximum radial dimension at the opposing end. This geometry aids in focusing particles of differing p/q ratio to a common focus on the main axis.

This is because beams of differing p/q ratio travel different distances through the magnetic field produced by the planar coils as a result of their geometry. For example, beams of relatively higher p/q ratio will typically enter the toroidal magnet at a radial location further from the primary axis than beams of relatively lower p/q ratio. The radial dimension of the coils varying along the length of the primary axis as described above means that the beams of higher p/q ratio travel further through the magnetic field and thus may be deflected through a greater angle in order that the beams are focused to a common point on the primary axis.

In a preferred embodiment, a radially outer portion of each planar coil is arranged (e.g. configured to be) substantially parallel with the main axis of the toroidal magnet, and a radially inner portion of the coil extends between the portion of the coil having the maximum radial dimension and the portion having the minimum radial dimension, such that the radial dimension varies along the elongate length of the coils. The radially inner portion of each coil may be curved (typically convex) such that the radial dimension of each coil varies along the elongate length, although in other embodiments the radially inner portion may be substantially linear or comprised of a plurality of linear and/or curved sections.

Such geometry finds particular advantage in embodiments where the gantry comprises one (e.g. a single) toroidal magnet.

In general, the geometry of the toroidal magnet coils can be shaped to adapt the integrated field length to the required range of beam momentum to charge ratios.

Each coil comprises a plurality of windings (or "grades") through which current flows in order to produce the desired magnetic field. In one configuration, the windings substantially abut each other in a radial direction, and the magnetic field profile has a 1/R dependence. Such a configuration is referred to as having no geometric grading. Advantageously, the geometric configuration of the windings may be configured to change the magnetic field profile to a 1/R" dependence, where n is defined as the field index. This may be done by spacing the individual windings of a coil, preferably in the radial direction. The spacing of the windings is referred to as geometric grading, and can be advantageously used to control the magnetic field as desired.

The current density through the windings may also be varied in order to manipulate the magnetic field profile, and this is referred to as current grading.

At the radially outer part of the toroidal magnet, the field leakage in the inter-coil space causes the field lines to bend (referred to as "field pinching"). This produces a field component that tends to bend a beam initially off the symmetry plane between two adjacent coils towards the symmetry plane, and adds to the natural focusing effect of the toroidal magnet. (It is to be noted that the field is still periodically symmetric about the primary axis.) The amount of field curvature can be controlled acting on the geometry and location of the outer portions of the coils. In particular, the amount of curvature (or "pinching") of the field can be modified by:

grading the coil in a toroidal direction;
adding a secondary "correction" coil adjacent the main coil to introduce quadrupole (linear field dependence in space) and higher order correction field terms such as a sextupole (parabolic field dependence in space), or;
using a coil comprising ferromagnetic material in order to adjust the field.

The coils of the toroidal magnet experience electromagnetic forces acting on them. These comprise "in-plane" forces acting on the coil winding itself, which act in the plane of each coil and are directed in a radially outward direction (i.e. tending to push each coil outwards), together with a larger (and therefore resultant) radially inwards force that tends to push all of the coils inwards towards the main axis. In addition, in the case of imbalanced currents, the coils experience "out of plane" forces acting in the toroidal direction that tend to "fold" the coils of the magnet.

Therefore, the gantry preferably comprises a support structure adapted to support the plurality of planar coils, wherein the support structure is configured to allow the passage of the beam of charged particles through the gantry in use. The support structure supports the coils of the magnet against the electromagnetic forces acting on them whilst simultaneously allowing the passage of charged particles through the gantry. In use, a beam of charged particles enters the toroidal magnet through one of its ends (where the magnet extends between two opposing ends positioned along the primary axis), and is deflected by the magnetic field such that it exits the magnet into the central bore towards the primary axis (preferably at 90 degrees to the primary axis). The support structure therefore preferably comprises at least one aperture at a radially inner part thereof such that a beam of charged particles can pass into the central bore. Preferably the support structure comprises a plurality of apertures which are positioned in a toroidally periodic manner corresponding to the trajectories of beams travelling through the periodically symmetric magnetic field.

For example, the support structure may comprise a bucking structure positioned within the central bore against which the radially inner portions of the coils are supported ("buck") against the resultant radially inwards force, with such a bucking structure comprising at least one aperture or window for the passage of the charged particles into the central bore. The bucking structure may be either physically continuous along the primary axis (e.g. in the form of a bucking cylinder), or formed by the assembly of wedged noses in the coil structure. Preferably, such a bucking structure comprises a plurality of toroidally periodic apertures or windows for the passage of the beam into the central bore. The use of such a support structure allowing the beam of charged particles to travel into the central bore is an innovative arrangement that is not required in conventional uses of toroidal magnets, and further highlights the unconventional use of a toroidal magnet in the present invention.

It is to be noted that the beams of charged particles will travel through the gantry within a beam vacuum pipe or vacuum chamber, and as such the support structure will need to accommodate said vacuum pipe or chamber. Preferably the beams will travel through a static vacuum chamber installed within the gantry.

The gantry preferably comprises a single toroidal magnet, but in embodiments may comprise two or more such magnets dependent on the desired beam trajectories and configuration of the gantry.

In embodiments where the gantry comprises two or more toroidal magnets, typically each toroidal magnet shares a common primary axis. Furthermore, in such embodiments the beams of charged particles having different momentum to charge ratios are typically focused to a common point on the primary axis after having travelled through each of the toroidal magnets within the gantry. In other words, in particle therapy implementations for example, the subject may be positioned within the central bore of the most downstream toroidal magnet. In such embodiments, each of the two or more toroidal magnets preferably comprises a plurality of discrete, substantially planar coils spaced apart and extending radially from the primary axis. The geometry of the two or more toroidal magnets typically differs such that the combined forces acting on the particle beams due to the magnetic fields of the toroidal magnets allows the focusing of the beams to a common point on the primary axis.

Typically, the toroidal magnet (e.g. gantry) is configured to receive beams of higher momentum to charge ratio (higher energy) at a more radially outward location as compared to beams of lower momentum to charge ratio (lower energy). However, this is not necessarily the case, as will be discussed in more detail herein.

In accordance with a second aspect of the invention there is provided an apparatus for focusing charged particles, comprising: a bending device configured to receive beams of charged particles, and; a gantry according to the first aspect of the invention, wherein the bending device is configured to direct beams of charged particles towards the gantry dependent on the momentum to charge ratios of the beams such that beams of charged particles having different momentum to charge ratios are directed towards a common point on the primary axis of the gantry.

Preferably the primary axis of the gantry and the primary axis of the at least one toroidal magnet coincide (i.e. are the same axis). The bending device is typically positioned spaced from the gantry (toroidal magnet) along the primary axis.

The bending device is typically configured to direct the beams of charged particles towards the gantry (e.g. at least one toroidal magnet) at a non-zero angle with respect to the primary axis.

The bending device is configured to receive beams of charge particles, typically from a particle accelerator, with the extracted beam from the accelerator being provided to the bending device. The bending device is configured to deflect an extracted beam in any direction by an angle that depends on the beam energy. For gantry coil geometries, in order for beams of differing p/q ratio to be focused to a common point on the primary axis, the angle of deflection (with respect to the main axis) generated by the bending device is typically configured to increase with beam energy.

In preferred embodiments, the bending device is configured to deflect a beam of charged particles having momentum p and charge q towards the gantry at an angle $\alpha_E$ to the primary axis given by:

$$\alpha_E = \arcsin\left(\frac{\rho_E(z_V - \rho_E) + R_{in}\sqrt{R_{in}^2 + z_V^2 - 2z_V\rho_E}}{(z_V - \rho_E)^2 + R_{in}^2}\right)$$

where $$\rho_E = \frac{p}{qB_0}$$

$Z_v$ is the distance, along the primary axis, between the bending device and the ultimate point of focus of the charged particle beams, and $R_{in}$ is the inner radius of the toroidal magnet (i.e. the distance between the primary axis and the radially inner part of a coil). Typical values of $Z_v$ are in the range of 1 m to 10 m, preferably 4 m.

Thus, typically, beams of higher p/q are deflected through a larger angle by the bending device and enter the gantry (e.g. toroidal magnet) at a larger radial location (i.e. radially further from the primary axis) than beams of lower p/q. However, this is not always the case, and in other implementations (for example where the gantry comprises two or more toroidal magnets), beams of higher p/q may be deflected through a smaller angle by the bending device than beams of lower p/q such that beams of higher p/q enter the gantry at a smaller radial location (i.e. radially closer to the primary axis) than beams of lower p/q. In general, beams of a particular momentum to charge ratio are deflected by the bending device through an angle dependent on the configuration (e.g. geometry) and number of toroidal magnets within the gantry so as to allow focusing to a common point on the primary axis.

The bending device may be any device that suitably deflects an extracted beam of charged particles, such as bending crystals or a plasma. However, in preferred embodiments, the bending device is a vector magnet, preferably a rotating single dipole magnet, a two axis dipole magnet or a quadrupole. The use of a two axis (e.g. horizontal and vertical) dipole magnet or quadrupole is particularly desirable as in such a case the whole apparatus (i.e. the bending device and the gantry) has no moving parts, which is a significant departure from state-of-the-art configurations, particularly in charged particle therapy.

Typically the vector magnet comprises one or more resistive magnets. The vector magnet function can be achieved with a single magnet, or a sequence of magnets with adapted aperture that have single plane or combined plane functions, and can act as trim or scanners.

Thus, the invention includes an apparatus (e.g. system) for focusing beams of charged particles having differing momentum to charge ratios to a substantially common point, the apparatus comprising: a bending device configured to receive beams of charged particles; and a gantry comprising at least one toroidal magnet having a central bore, a primary axis of the toroidal magnet extending along the central bore, the toroidal magnet configured to receive beams of charged particles at different radial locations dependent on the momentum to charge ratio of the beam; wherein the toroidal magnet comprises a plurality of discrete, substantially planar coils spaced apart and extending radially from the primary axis and configured to produce a magnetic field such that, in use, beams of charged particles having respective components of motion along the primary axis and entering the toroidal magnet (e.g. gantry) at different radial locations are directed towards a common point on the primary axis, wherein the planar coils are configured to produce a magnetic field that is periodically symmetric about the primary axis, and; the at least one toroidal magnet is substantially stationary in use, and wherein; the bending device is configured to direct beams of charged particles towards the gantry dependent on the momentum to charge ratios of the beams such that beams of charged particles having different momentum to charge ratios enter the gantry at different radial locations and are directed towards a common point on the primary axis.

The gantry or apparatus of the present invention is preferably for use in charged particle therapy, and wherein, in use, a subject is positioned within the central bore of the at least one toroidal magnet. Advantageously, the gantry is typically stationary in use.

BRIEF DESCRIPTION OF THE DRAWINGS

Preferred embodiments of the invention will now be described with reference to the drawings, in which:

FIG. 19 schematically illustrates a gantry comprising two toroidal magnets;

DETAILED DESCRIPTION

System Concept

Figure 1:
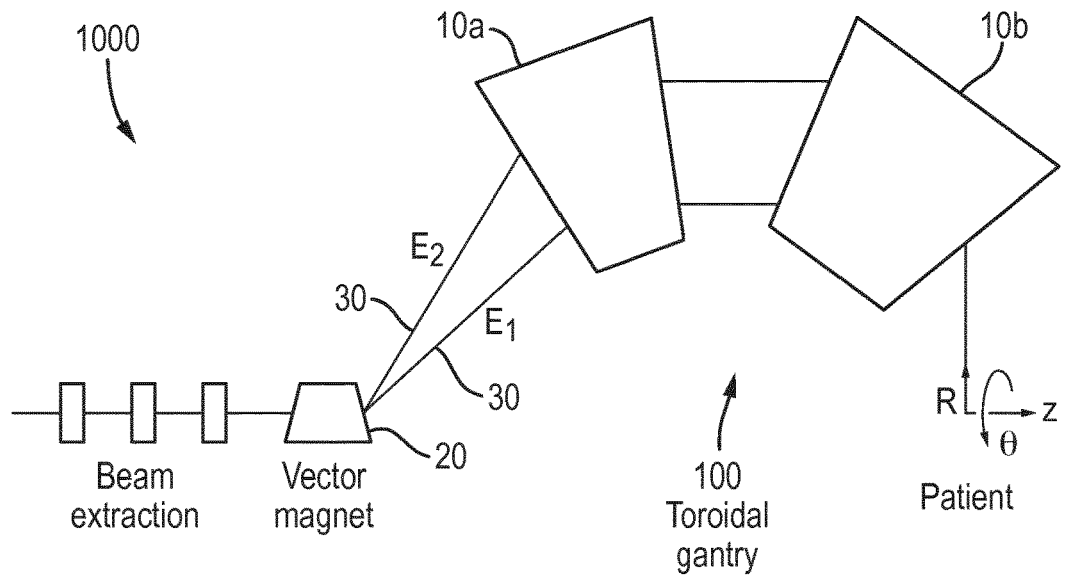
FIG. 1 is a schematic illustration outlining the concept of the invention.

The concept of the apparatus for charged particle therapy (1000) according to the invention is shown in FIG. 1. It consists of two main parts: a vector magnet 20 and a gantry 100 comprising one or more toroidal magnets 10.

The vector magnet 20 is configured to receive a beam of charged particles from a particle accelerator extraction line, and provide a deflection to the beam that depends on the energy of the beam and the desired direction of delivery.

The one or more toroidal magnets (two magnets 10a, 10b are depicted in FIG. 1 as an example, with only one coil of each magnet shown for clarity) steer the deflected beam 30 by using a combination of their shape and field variation with radius and length. In FIG. 1, ideal beam trajectories are represented for two different beam energies (E2>E1), with both beams being focused on the same point.

A key aspect of the apparatus is the use of the axis-symmetric field generated by the toroidal magnet(s) of the gantry.

The function of the vector magnet 20 is to deflect the extracted beam in any direction by an angle that depends on the beam energy. For a given energy this corresponds to the ability to produce a cone of beam trajectories originating at the vector magnet 20. For practical toroidal magnet shapes and field profiles (as will be discussed below), the bending angle is required to increase with energy. The vector magnet 20 hence directs the beam in concentric cones.

The vector magnet 20 can be a single dipole rotating around its axis with the ability to sweep the field strength. In this case a change in field strength is required to steer beams of different energy, and is preferably frequent and fast (of the order of fractions of second). A rotation, on the other hand, corresponds to a change in irradiation direction, and can be sporadic and much slower (of the order of several seconds). Alternatively a two-axis vector magnet may be used, producing a combination of horizontal and vertical dipole with arbitrary direction. If this option is selected, the two dipoles need to change frequently, rapidly and in synchronization.

The actual bending angle of the charged particle beam 30 entering the gantry 100 depends on the integrated field strength of the magnet(s) 10, which can be modulated by a control of the magnet dimension, shape, and placement of the conductors. In this discussion we start from an ideal, axis-symmetric toroidal field, generated by a thin current winding around the torus. This produces a toroidal field $B_\theta$, of module:

$$B_\theta = \frac{B_0 R_0}{R} \quad (1)$$

where R is the radius measured from the axis of the toroid, and $B_0$ and $R_0$ are constants determined by the location and current in the winding. For this discussion we take $B_0$ to be the peak field, obtained at the inner radius of the toroid $R_0$. The field is zero in the inner space of the toroid, i.e. for a radius $R<R_0$. This is the space where the subject is located for charged particle therapy.

To illustrate the working principle, we demonstrate below the effect of a toroidal magnet on charged particles of variable momentum to charge ratio p/q. We define to this aim a reference frame consisting of the direction z aligned with the centre of the toroidal magnet, the radial direction R originating on the axis z, and the toroidal direction $\theta$ that defines the angle around the z axis (see FIG. 1).

The ideal toroidal field is given by Eq. (1) in a region of space $z_{min}<z<z_{max}$ (i.e. the length of the gantry 100) and $R<R_0$. We break the general problem of particles entering the toroidal field area with arbitrary p/q into the two separate effects of the field seen by particles traveling in the (R,z) plane (in-plane beam), and of the field seen by particles traveling in an arbitrary direction containing also a $\theta$ component (out-of-plane beam).

For in-plane beams we can track the particle trajectory by using the simple relation:

$$B_\theta = \frac{p}{q} \quad (2)$$

where p is the curvature radius of the bent beam in the (R,z) plane. The momentum is defined using the relativistic relation:

$$p = E_0 \sqrt{\gamma^2 - 1} \quad (3)$$

where $E_0$ is the rest energy of the particle (or ion) considered, and $\gamma$ is the relativistic factor:

$$\gamma = 1 + \frac{E_K}{E_0} \quad (4)$$

defined by the kinetic energy $E_K$ of the particle.

Figure 2A:
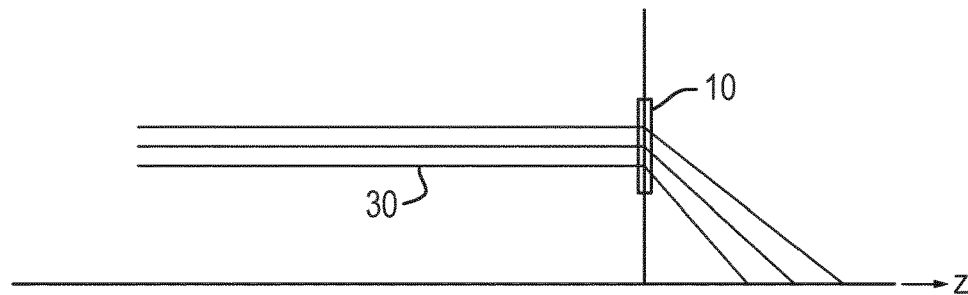
FIG. 2(a) shows the effect of a thin toroidal field lens on parallel beams with the same energy.
Figure 2B:
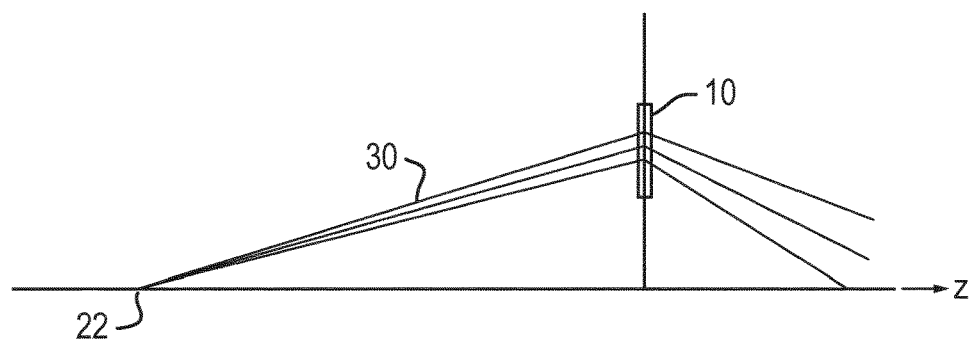
FIG. 2(b) shows the effect of a thin toroidal field lens on beams with the same energy and originating at the same vertex, but with different divergence.

The effect of a thin toroidal field magnet 10 (a thin toroidal lens) is shown in FIG. 2a for a parallel beam of particles 30 of identical momentum and charge, but different position, as well as for a beam 30 originating at a vertex, but different divergence (FIG. 2b). Each track corresponds to a particle in the beam 30. The thin toroidal lens 10 has a net focusing effect, but the natural dependence of the ideal toroidal field on the radius results in a strong astigmatism, as shown by the beam failing to come to a single focus after passing through the lens.

Figure 3A:
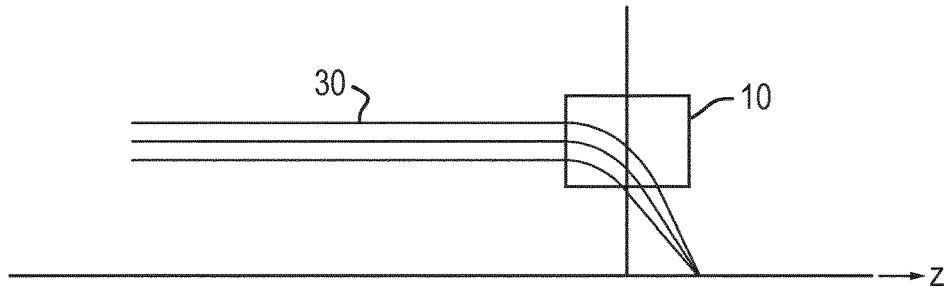
FIG. 3(a) shows the effect of a thick toroidal field lens on parallel beams with the same energy.
Figure 3B:
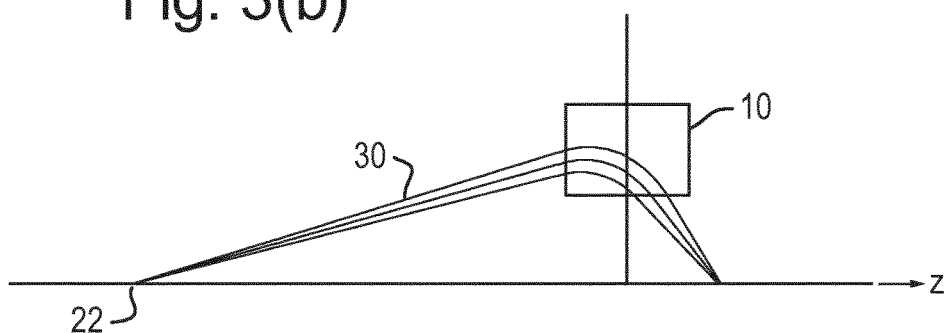
FIG. 3(b) shows the effect of a thick toroidal field lens on beams with the same energy and originating at the same vertex, but with different divergence.

On the other hand, if we take into account that the size of the region with the toroidal magnet is significant with respect to the variation of the beam orbit (a thick toroidal lens) we notice that the astigmatism is much reduced. This effect is shown schematically in FIGS. 3a and 3b, where again each track corresponds to a single particle in the beam 30. The reduced astigmatism is due to the fact that particles entering with large orbit or large angle travel a longer path in the magnetic field than particles entering at small orbit or angle, thus resulting in additional focusing. The same effect holds for both parallel and divergent beams of the same momentum, and is dependent on the geometry of the toroidal field area.

Figure 4:
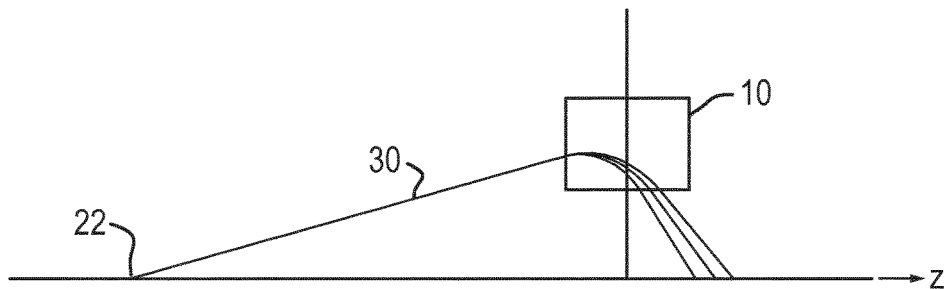
FIG. 4 illustrates the effect of a thick toroidal field lens on beams with different p/q originating at the same vertex and with the same initial angle.
Figure 5:
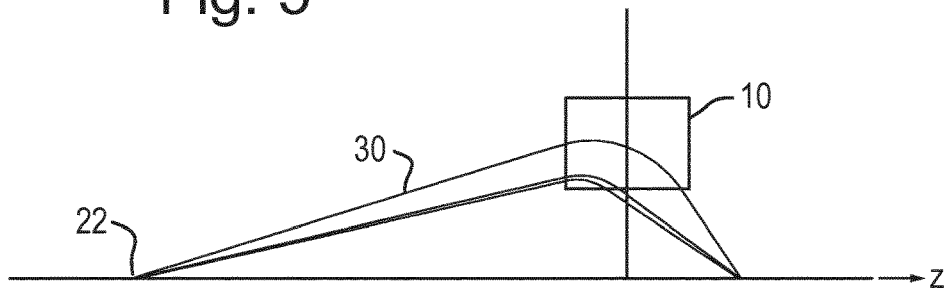
FIG. 5 illustrates the effect of a thick toroidal field lens on beams with different p/q originating at the same vertex and with different angles.

We now examine the case of the beam momentum (or more in general the p/q ratio) on the focusing effect of a thick toroidal lens. This is shown schematically in FIG. 4, where now the tracks correspond to beams originating at the same vertex (22), with the same angle, and a variation of p/q of approximately 15%. Beams with higher rigidity are bent less—beams with a higher p/q ratio are focused to further distances along the z axis. However, taking into account the observation above on the focusing effect of the length travelled in the region of magnetic field, it is possible to find appropriate initial angles for each of the beams in the selected range such that the focal point on the z-axis is the same for all values of p/q. This is demonstrated in FIG. 5, where three beams of different p/q are deflected by different amounts at the vertex 22, enter the thick toroidal lens 10 at different points, and are eventually focused to the same focal point on the z axis due to different path lengths through the toroidal lens.

Figure 6:
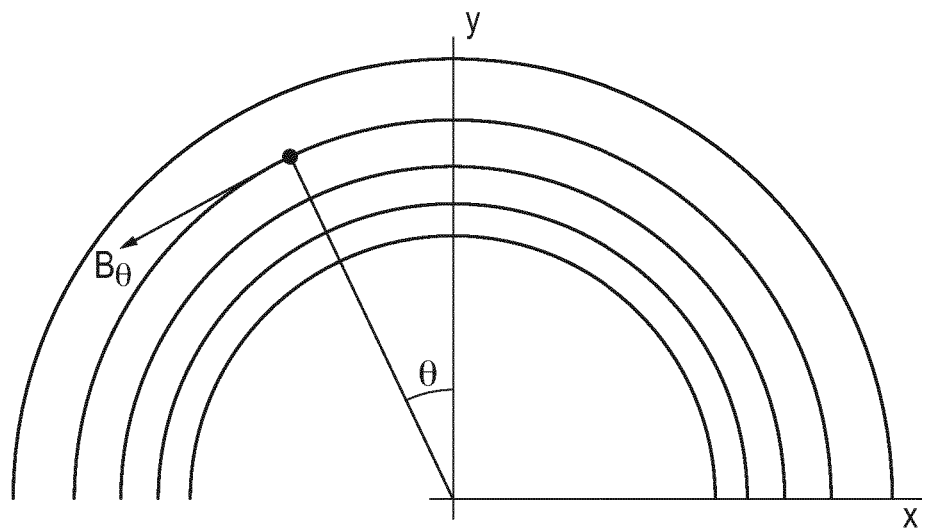
FIG. 6 illustrates the geometry for calculating the field gradient experienced by a charged particle entering the toroidal field at an arbitrary angle.

We now look at the case of particles with momentum components out of the (R-z) plane. Considering a particle entering the toroidal magnetic field at a position (x,y) corresponding to an arbitrary angle $\theta$ (see FIG. 6), the magnetic field seen by the particle will have a component Bx given by:

$$B_x = B_\theta \sin(\theta) \quad (5)$$

For small angles this corresponds to a gradient that tends to focus the particle back to the axis of the toroid. Given the ideal dependence of the toroidal field on the radius (see Eq. (1)), the focusing quadrupole has a decreasing intensity as the radius increases.

Following this brief (non-exhaustive) summary of the concept of the invention, we will now describe a preferred embodiment of the invention.

Design of the Toroidal Magnet

Drawing from the considerations in the previous section, we will now discuss the design of a toroidal magnet for use in the present invention. We take as a relevant example a proton beam with energy range of 70 MeV to 250 MeV that may be used for charged particle therapy. The design principle applies directly to any p/q ratio.

Coil Geometry

For the purposes of this discussion we assume that the gantry 100 comprises one toroidal magnet 10 comprising a plurality of discrete substantially planar coils 1, receiving a beam 30 deflected to an arbitrary angle by a vector magnet 20. We assume that the magnet 10 has a coil shape optimized to generate a magnetic field for providing the desired bending effect on the beam 30. The focusing point is taken at (0,0) along the z axis, while the vector magnet 20 is placed at $(0,-z_v)$. We take as a constraint that the beam exiting the gantry 100 must directed at 90 degrees to the subject. The toroidal magnet 10 has an inner free bore of radius $R_{in}$.

For the field shape, we make the assumption that the coil 1 is graded so to generate a constant field $B=B_0$ (i.e. n=0) in the inter-coil space. This can be achieved spacing the turns radially in the inboard side of the toroid, as will be discussed below.

A final assumption we make is that the field has sharp boundaries, i.e. $B=B_0$ within the perimeter of the toroidal magnet, and $B=0$ elsewhere.

We can now reconstruct the contour of an ideal toroidal magnet 10 that achieves the desired focusing properties. To illustrate this we use the geometry shown in FIG. 7. Starting from the origin location (0,0) at where the beams are desired to be focused, we can trace back the beam trajectory. The beam travels in a radial direction first, until it enters the toroidal field area at a radius $R_{in}$. Once in the toroidal field it is bent with a constant radius, following Eq. (2):

$$\rho_E = \frac{p}{qB_0} \quad (6)$$

The simplest solution for the field contour is the location of the circle given by Eq. (6), tangent to the straight line coming from the vector magnet 20 (see FIG. 7). The angle ($\alpha_E$) corresponding to the optimal direction of the beam with respect to the z axis can be computed as follows:

$$\alpha_E = \left( \frac{\rho_E(z_V - \rho_E) + R_{in}\sqrt{R_{in}^2 + z_V^2 - 2z_V\rho_E}}{(z_V - \rho_E)^2 + R_{in}^2} \right) \quad (7)$$

In fact, if the position of the vector magnet 20 is sufficiently far from the gantry 100, the above expression can be simplified as follows:

$$\alpha_E \approx \frac{R_{in} + \rho_E}{z_V - \rho_E} \quad (8)$$

Figure 7:
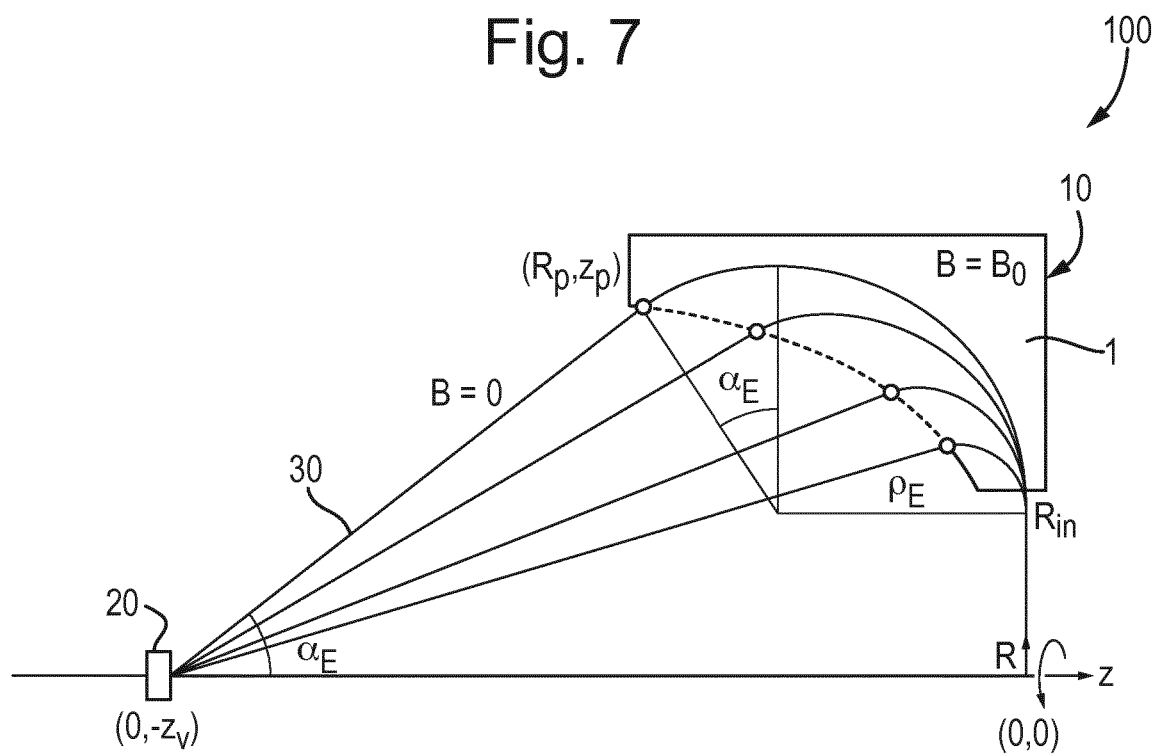
FIG. 7 illustrates the construction of an ideal field profile of a toroidal field boundary that focusses beams of different p/q to a single focal point.

Equation (8) is a good initial approximation for an ideal magnet contour for use in the invention, delimiting the entry perimeter of the beam in the shaded area of FIG. 7. FIG. 7 illustrates the construction of the ideal profile of a toroidal field boundary that focuses beams of different momentum to charge ratio p/q on a single focal point by making use of different deflection angles at the location of the vector magnet 20. The toroidal field area is shaded in the Figure. The dashed boundary can be computed using Eq. (7) or Eq. (8).

The above relations are applied next to the design of the winding of a toroid.

Magnet Parameters

In this example, we take a value of $B_0=3$ T for the field strength. This is a modest field value suitable for both low temperature and high temperature superconducting materials that may be used for the magnet windings. Noting that the momentum to charge ratio p/q can be scaled proportionally to the field, the design considered here applies to a carbon gantry provided that the field is scaled by a ratio 2.7 (the ratio of beam rigidity from protons to carbon ions in the desired energy range), i.e. a field $B_0=8.1$ T.

The bending radius for a beam energy of 250 MeV, is $\rho E=0.8$ m. Assuming an inner bore radius of the toroidal magnet of $R_{in}=0.4$ m (i.e. a subject space of 0.8 m diameter at the coil), and given the geometrical considerations in FIG. 7, the outer radius of the magnet 10 will be in the range of 1.2 m, which is very compact. The vector magnet 20 may be placed at a distance of 4 m from the gantry 100 (i.e. at (0,−4,) along the z axis), reasonably far away from the toroidal magnet to limit the magnet strength, but still maintain a compact overall size of the apparatus 1000.

Figure 8:
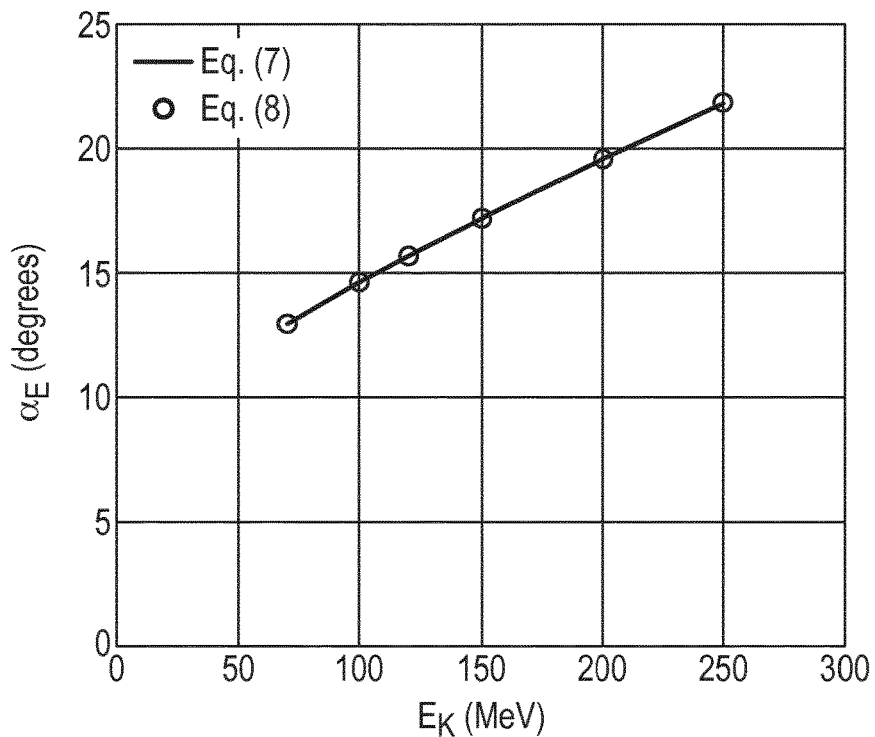
FIG. 8 is a graph of the optimal angle given by a vector magnet to obtain iso-centric focusing of proton beams of different kinetic energies in the range 70 MeV to 250 MeV.
Figure 9:
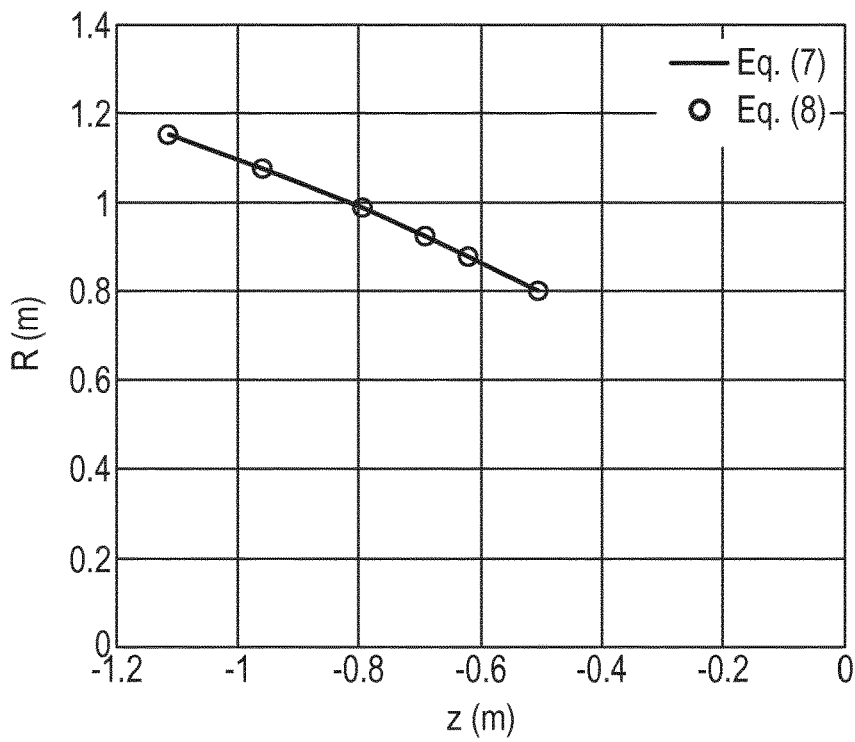
FIG. 9 is a graph illustrating the ideal radially inner ("inboard") profile of a toroidal field coil to obtain iso-centric focusing of proton beams of different kinetic energy in the range 70 MeV to 250 MeV.

With the above hypotheses, the optimal angle and the ideal contour of the toroidal coil leg at the entrance of the beam derived from Eq. (7) and the approximation Eq. (8) are plotted in FIGS. 8 and 9. We note that with this choice of parameters the coil contour is nearly straight, and the angle dependence on the kinetic energy of the beam is also approximately linear. Though not essential, these features offer the benefit of easy coil winding, and simple operation.

The computed coil contour for the beam entry point is completed by extending the toroidal coil to the inner radius of 0.4 m, and adding return legs. These are taken straight for simplicity, although it is envisaged that the return legs may be shaped to achieve a minimum volume envelope.

Figure 10A:
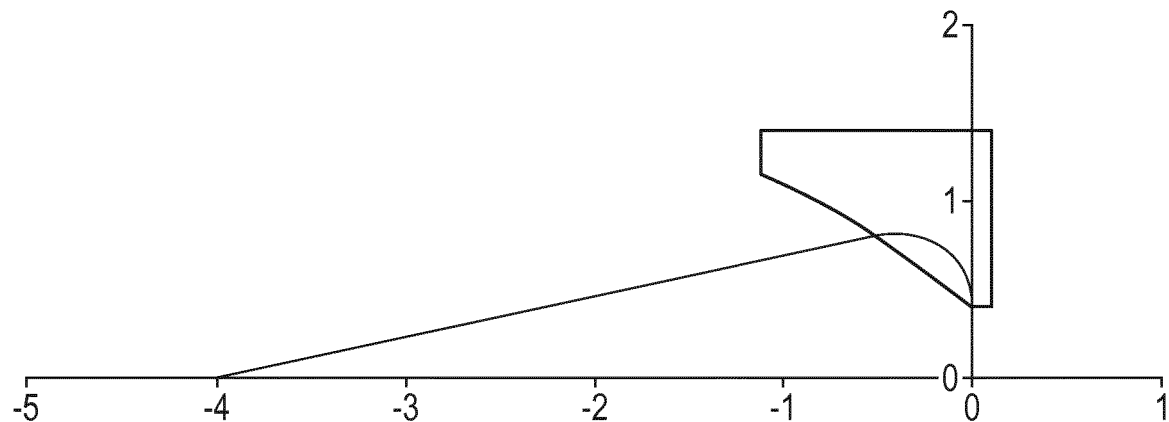
FIGS. 10(a) and 10(b) schematically show ideal toroidal field coil shapes, and example iso-centric focusing of proton beams of different kinetic energies of 70 MeV and 250 MeV.
Figure 10B:
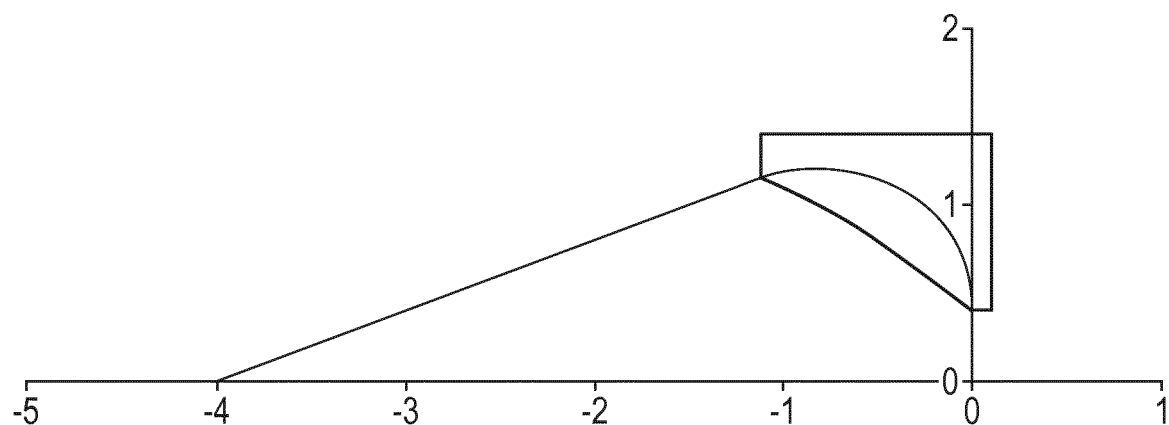

The resulting ideal coil shape is shown in FIG. 10, which also show the trajectories of two beams at the extreme of the beam energy range considered, with the lower energy beam (e.g. 70 MeV) shown in FIG. 10*a*, and the higher energy beam (e.g. 250 MeV) shown in FIG. 10*b*. The charged particle beams are bent by the magnetic field of the toroidal magnet 10, arriving at the patient at a 90 degrees angle.

Magnet Design

Figure 11A:
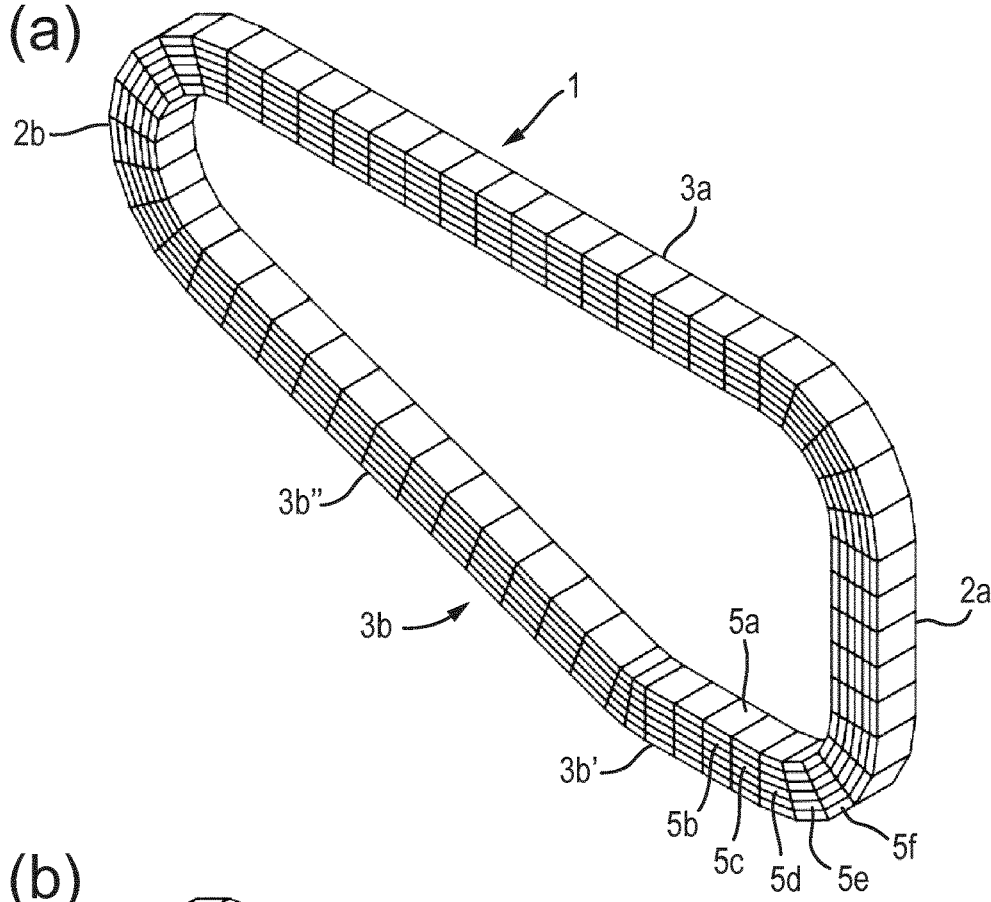
FIG. 11(a) illustrates a toroidal coil according to an embodiment of the invention.

Following the above considerations, FIG. 11(*a*) is a perspective view of a coil geometry that may be used according to an embodiment of the invention. As has been explained and illustrated above, in general the coil 1 comprises first 2*a* and second 2*b* radially extending portions that extend radially from the z axis (primary axis of the toroidal magnet 10), and first 3*a* and second 3*b* elongate portions extending between said radially extending portions. The first elongate portion 3*a* is at a radially outer position of the coil 1 and is substantially parallel with the z axis. The second elongate portion 3*b* is at a radially inner position of the coil 1. The first radially extending portion 2*a* is distal to the vector magnet, and the second radially extending portion 2*b* is proximal to the vector magnet. The first radially extending portion 2*a* is longer than the second radially extending portion 2*b*. The second elongate portion 3*b* is comprised of a first part 3*b*' substantially parallel to the z axis and a second part 3*b*" extending between the first part 3*b*' and the second radially extending portion 2*b* such that the radial dimension of the coil 1 varies along the z axis. As seen in FIG. 11(*a*), the coil 1 is substantially planar.

In FIG. 11(*a*), the coil 1 is split in six grades 5*a*, 5*b*, 5*c*, 5*d*, 5*e*, 5*f*. In this example, each grade has a dimension of 100 mm width by 20 mm thickness, and operates at an engineering current density of 200 A/mm². However, more than six, and fewer than six, grades are contemplated. Each grade operates at substantially equal current and the grades are packed in a single compact winding pack.

FIG. 11(*b*) illustrates a perspective view of a coil geometry according to an alternative embodiment. Here, the coil 1 still has all grades 5*a* . . . 5*f* operating at equal current, but also comprises a radial spacing between the grades 5*a*, 5*b*, 5*c* at the inner radius of the coil, with the objective to modify the radial dependence of the magnetic field.

The curved region required by equations (7) and (8) has been substituted by a straight part 3*b*" for simplicity of manufacture, although the second elongate part 3*b* may be formed in the curved manner required by equations (7) and (8). The outer coil dimensions in the examples shown in FIGS. 11(*a*) and 11(*b*) is approximately 1 m width by 2 m length.

Suitable materials for the coil 1 include both low temperature superconductors such as Nb—Ti and $Nb_3Sn$ and high temperature superconductors such as Rare Earth based (REBCO) and Bismuth based (BISCCO) Copper Oxides.

Figure 11B:
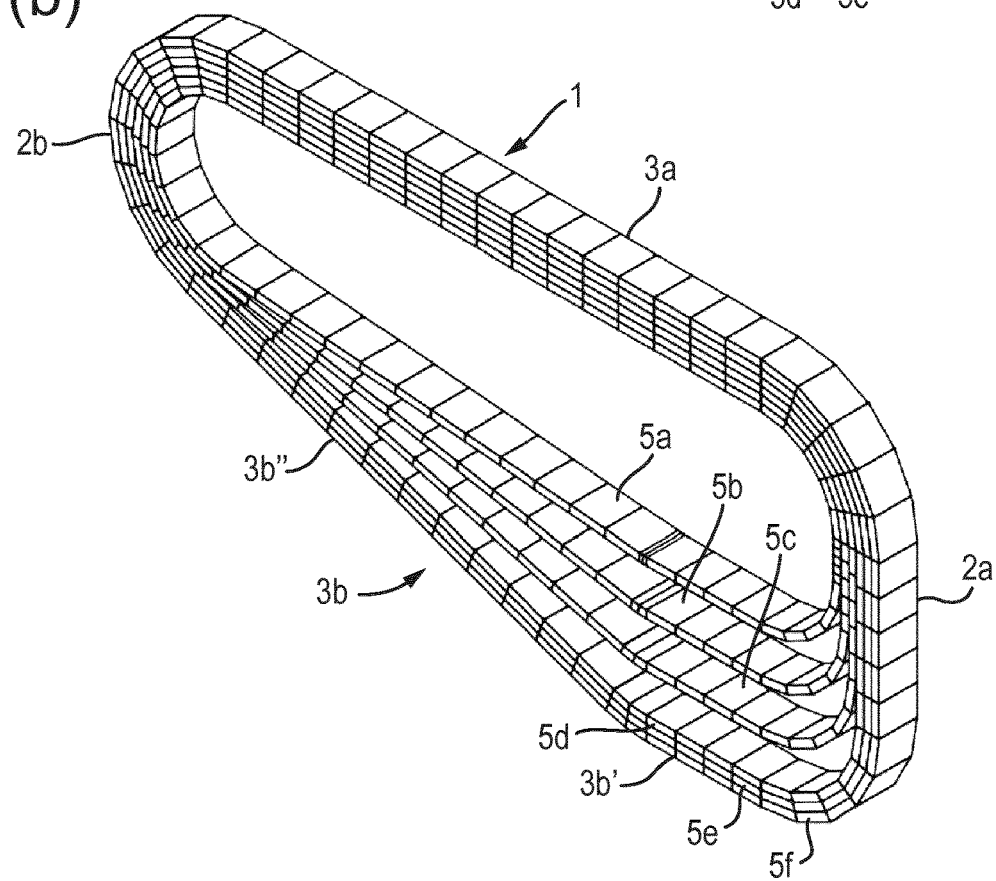
FIG. 11(b) illustrates a toroidal coil according to a further embodiment of the invention.
Figure 12:
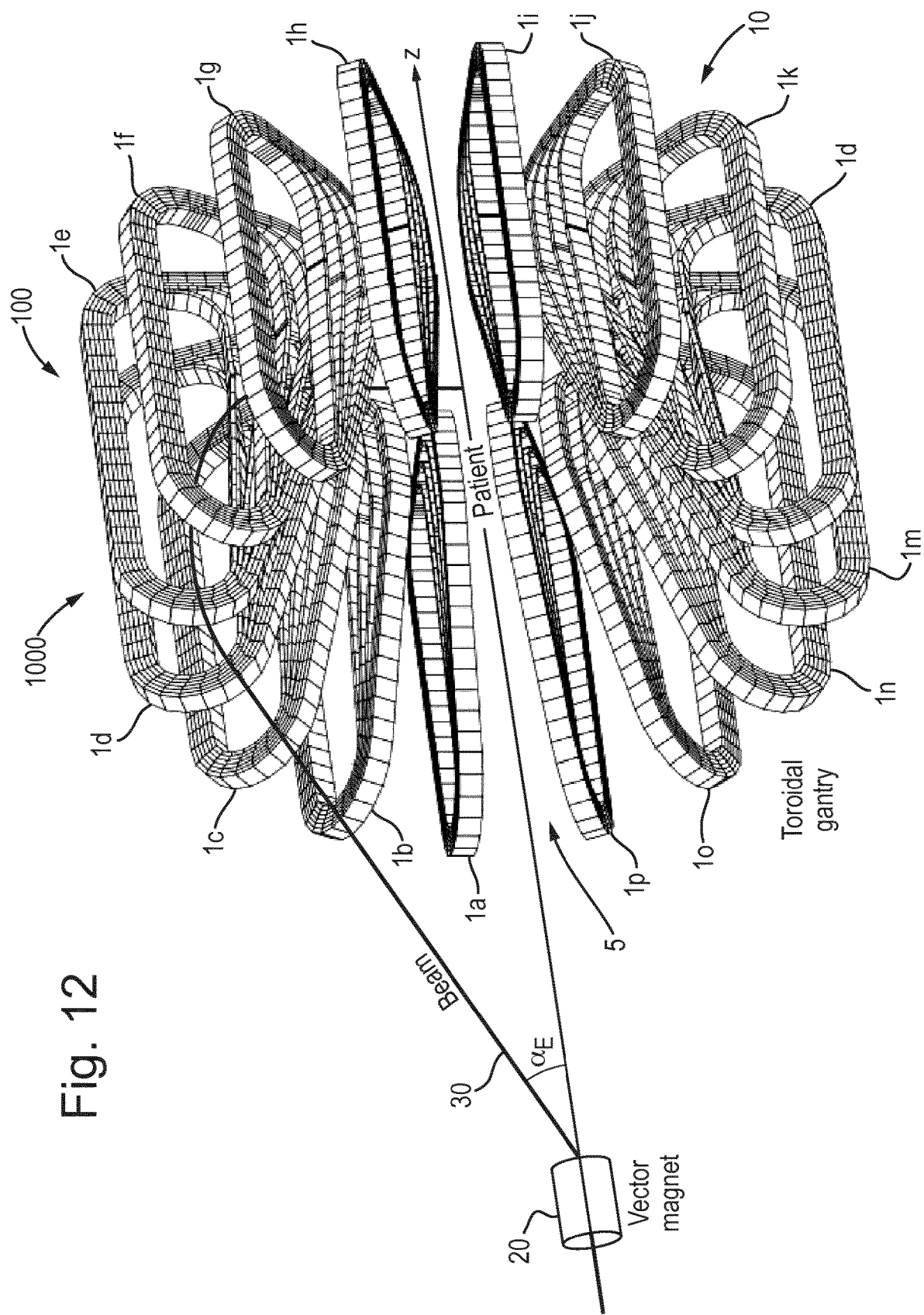
FIG. 12 is a schematic perspective view of an apparatus for charged particle therapy according to an embodiment of the invention.

FIG. 12 is a schematic perspective view of an apparatus 1000 for charged particle therapy according to an embodiment of the invention. The apparatus 1000 comprises a vector magnet 20 and a gantry 100. The gantry 100 comprises a toroidal magnet 10 which comprises 16 identical discrete planar coils 1a, 1b, . . . , 1p equally spaced apart and extending radially from the central bore 5 of the toroidal magnet 10. Each coil is as shown in FIG. 11(b). A primary axis (in FIG. 12 the z axis) of the toroidal magnet 10 is defined as extending along its central bore 5 of the magnet. The vector magnet 20 is positioned spaced from the gantry 100 along the z axis.

In use, a subject receiving charged particle therapy is positioned orientated along the z axis within the central bore 5 of the toroidal magnet 10, as illustrated in FIG. 12. A beam 30 of charged particles is provided to the vector magnet from a particle accelerator extraction line (not shown). The vector magnet 20 bends the beam 30 at an angle $\alpha_E$ to the z axis that is dependent on the beam energy, as explained above. The beam 30 enters the gantry 100 within the inter coil space between adjacent coils. A beam vacuum pipe (not shown) through which the particles travel is adapted to fit within this inter-coil space. Due to the magnetic field produced by the toroidal magnet, the charged particles are deflected and impinge on the subject, as schematically illustrated by the path of beam 30 in FIG. 12.

Figure 13:
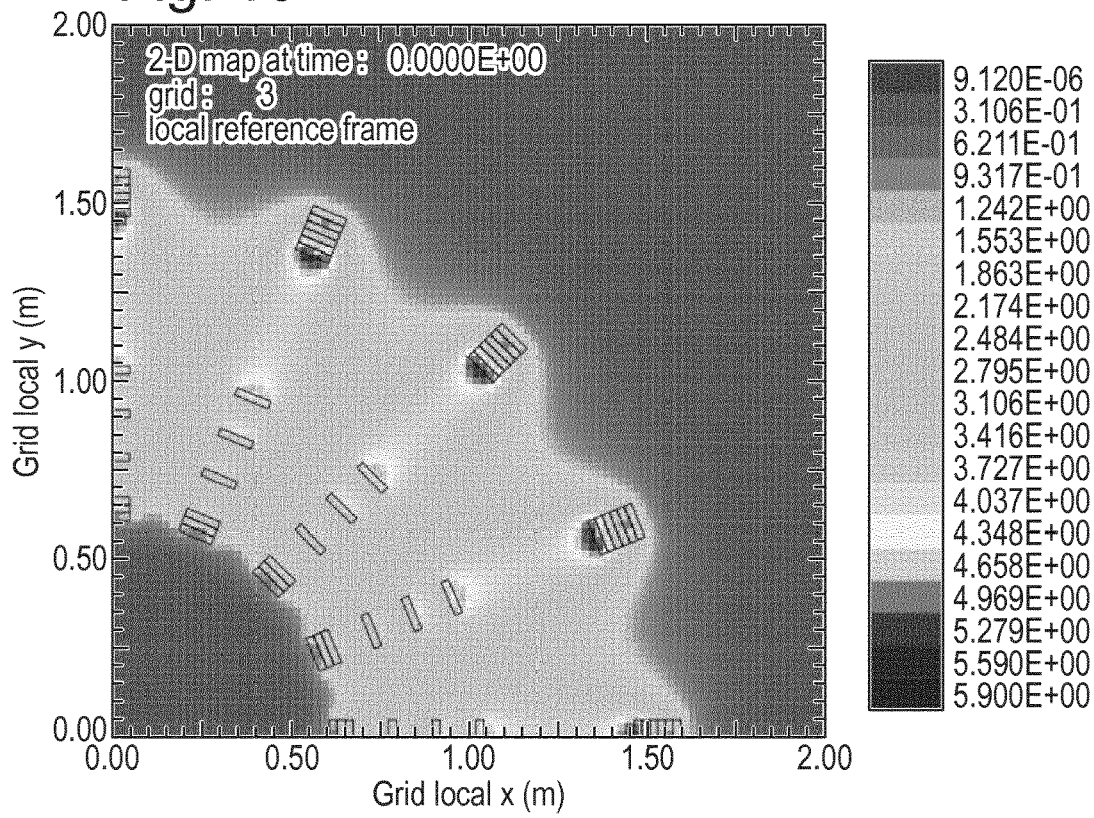
FIG. 13 is a map of the field intensity computed in a plane normal with the primary axis of the gantry, showing a quarter of the toroidal magnet.
Figure 14:
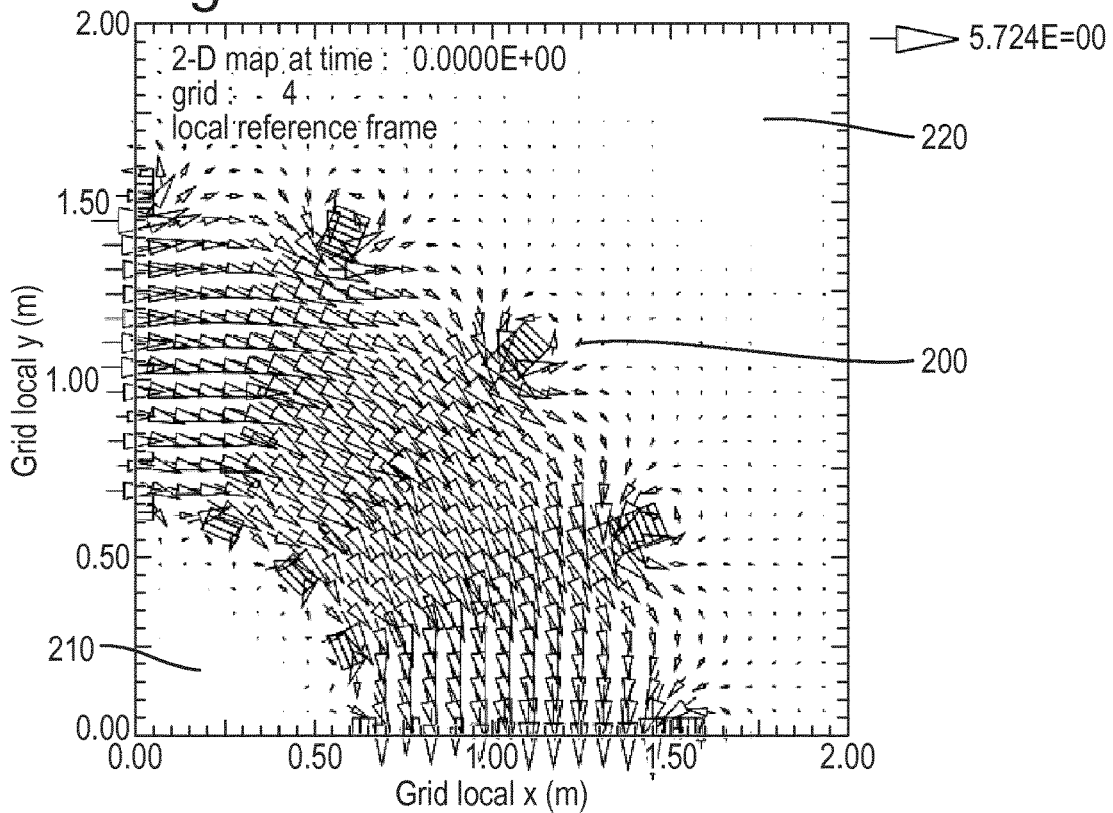
FIG. 14 illustrates the field vectors in the plane of FIG. 13.

The resulting map of the field intensity in a plane perpendicular to the z axis, and cutting the toroidal magnet 10 at a location along the z axis corresponding to the patient, is shown in FIG. 13. The associated field vectors are shown in FIG. 14. Besides the toroidal field value (approximately 3 T in this example) and general rotational symmetry, we note the pinching effect associated with the discrete number of coils. In particular, approaching the outer radius of the magnet 10, the field leakage in the inter-coil space causes the field lines to bend (note the direction of the field vectors at 200 in FIG. 14). This produces a field component that tends to bend a beam initially off the symmetry plane between two coils towards the symmetry plane, and adds to the natural focusing effect discussed earlier (see Eq. (5)). The amount of field curvature can be controlled acting on the geometry and location of the outer limbs of the coil. Note finally that the central region of the toroid (shown at 210) is, with excellent approximation, a field-free region (leakage field of few µT), which is a mandatory constraint for the subject area. Particularly advantageously, the field leakage outside the toroidal magnet is minimal (220), with acceptable field levels already at a few tens of cm from the outer radius.

Figure 15:
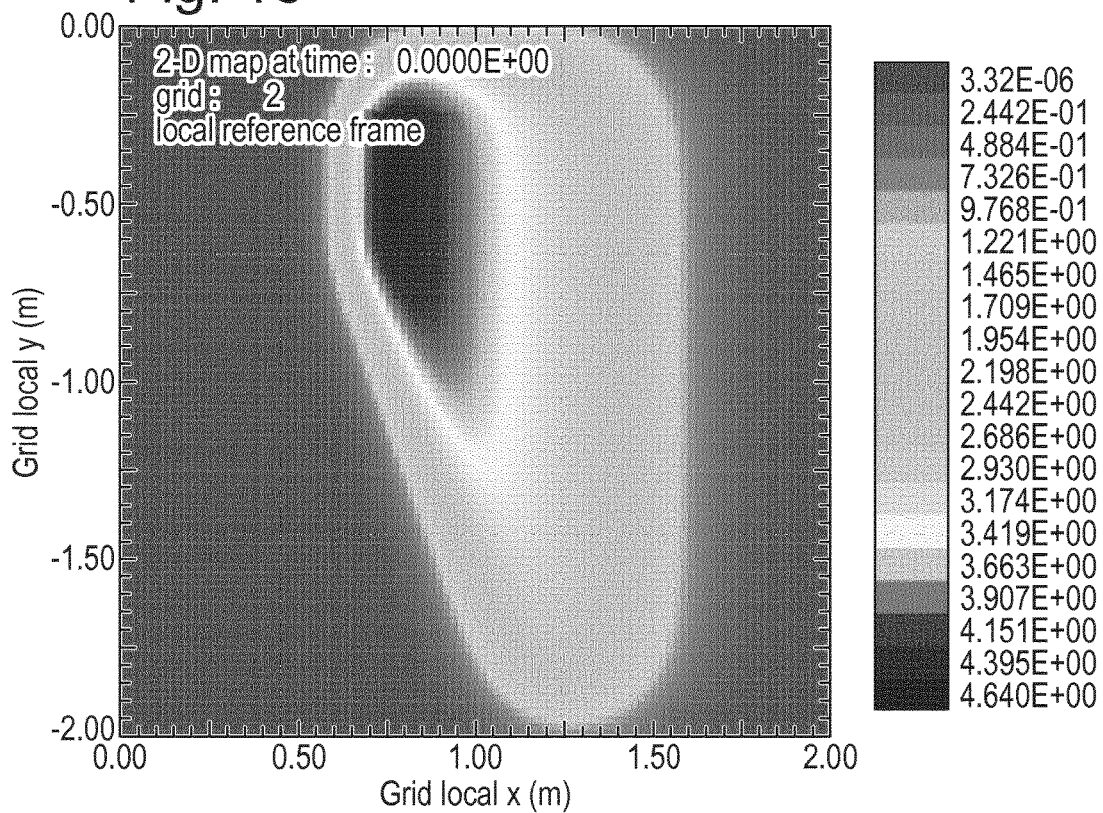
FIGS. 15 and 16 are maps of the magnetic field intensity computed in the symmetry plane between two neighbouring coils for non-graded and graded coils respectively.
Figure 16:
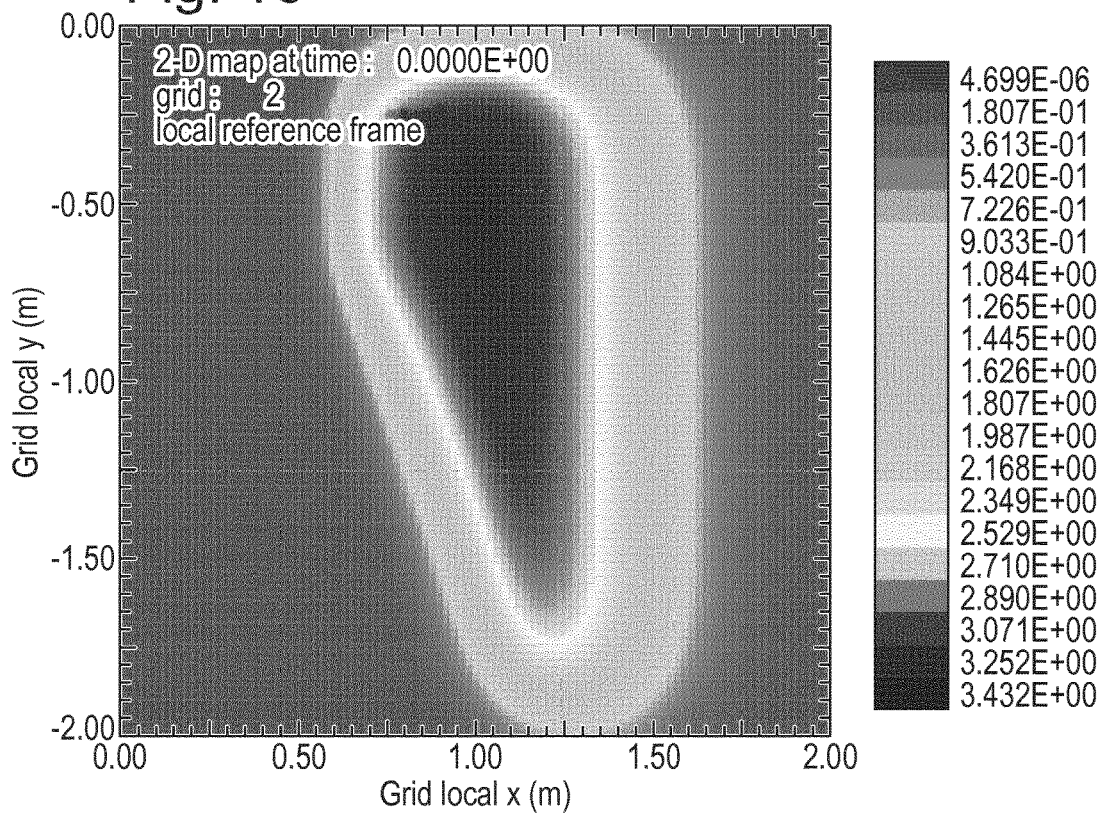
Figure 17A:
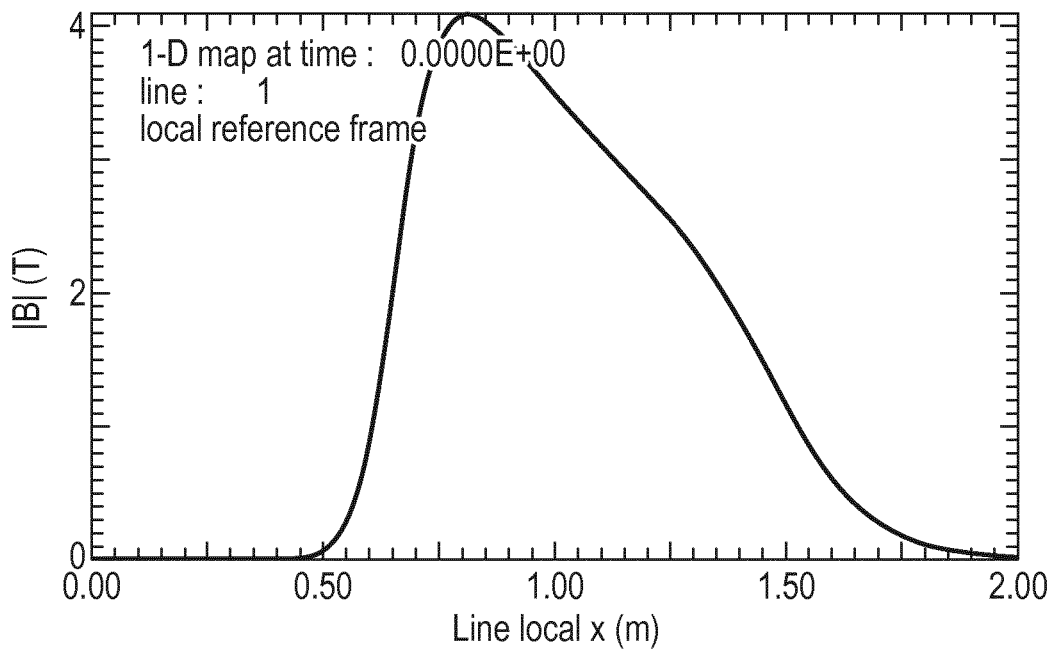
FIGS. 17(a) and 17(b) are graphs of the computed field intensity for the case of non-graded and graded coils respectively along a line originating at the location of the subject orientated radially and belonging to the symmetry plane between two coils.
Figure 17B:
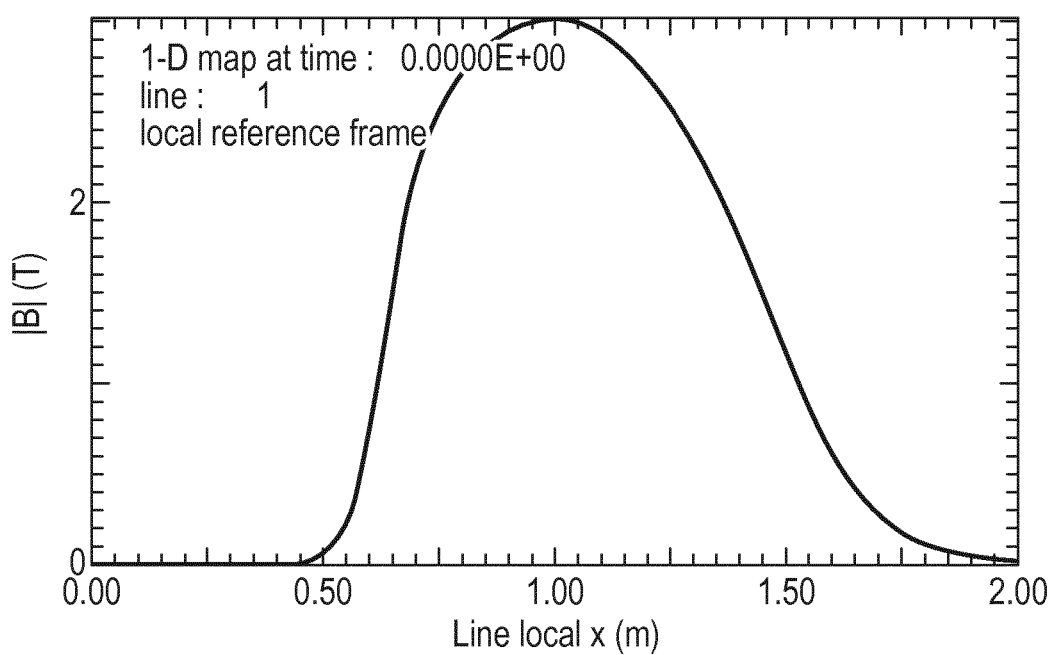

A map of the field intensity in the space between neighbouring coils, in the symmetry plane, is shown in FIGS. 15 and 16. We compare there the field in the case of the compact winding with no grading (FIG. 15), to the field produced by a geometrical grading (FIG. 16), i.e. the two coil options shown in FIGS. 11(a) and 11(b) respectively. The field of the graded coil is clearly more homogeneous, as shown in FIG. 16. This shows that the field index may be advantageously controlled by control of the coil geometry. A further comparison of the field profiles can be seen in FIGS. 17(a) and 17(b) which compare the modulus of the magnetic field computed along a line originating at the location of the subject, oriented radially and belonging to the symmetry plane between neighbouring coils. Advantageously, this illustrates that the gantry comprises enough degrees of freedom to adapt to particular requirements.

Given the magnet configuration, we can evaluate the electromagnetic forces exerted on the single coils 1 and in the gantry 100. In this example, the force exerted on the winding, tending to push the coil 1 towards the outside direction, has a maximum of 1 MN/m. To support this force each coil 1 comprises a casing structure (not shown) that hosts the complete coil, with a plate connecting the portions ("limbs") of the coil, as the coil space is not used. The coil leans on the outer band of the casing, and the average pressure on the winding is below 50 MPa.

The main net component in the toroidal magnet is a centering force (i.e. directed radially inward). The force per coil for the graded configuration of FIG. 11(b) described above is 1.5 MN. Although other solutions are envisaged, in the present embodiment a central bucking cylinder 500 (see FIG. 18) is used to react against this centering force. The bucking cylinder 500 comprises a plurality of apertures 510 for the passage of the beams of charged particles into the central bore 5, and subsequently onto the subject. The apertures 510 are positioned in a toroidally periodic manner so as to correspond to the trajectories of beams travelling through the periodically symmetric magnetic field. In other embodiments the bucking cylinder may comprise a single aperture extending circumferentially around the cylinder.

Figure 18:
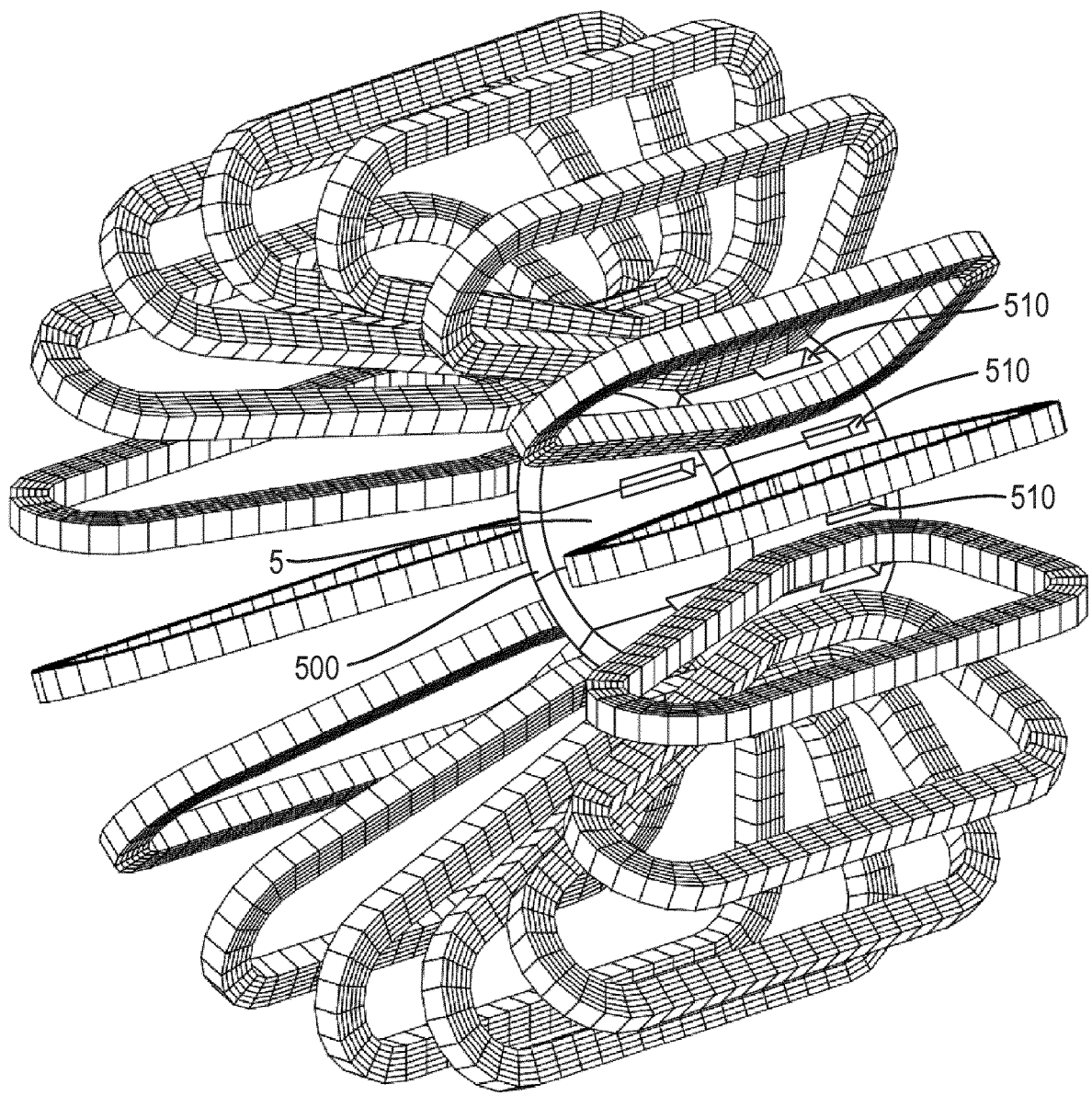
FIG. 18 illustrates a bucking cylinder used in an embodiment of the invention.

The bucking cylinder may be either physically continuous along the z axis as seen in FIG. 18, or alternatively formed by the assembly of wedged noses in the coil structure.

The thickness of the bucking cylinder required for this design is modest; for example a 100 mm thick structure of 1 m length would work at 30 MPa to react the centering force reported above. Advantageously, the gantry is therefore relatively lightweight.

The stored energy at nominal condition for the graded coil (FIG. 11(b)) configuration reaches 40 MJ for the whole toroidal magnet 10. This is a relatively large stored energy, and requires consideration of the design of the powering and protection system. For example, if the conductor is designed for 1 kA operation, and the magnet has a nominal dump voltage of 2 kV, a dump of the total magnet energy would take 40 s. This in turn would need a large amount of stabilizer, resulting in low operating current density. In a magnet of this type it is more advantageous to subdivide the circuit, so to reduce the stored energy in each part and the dump time. Maintaining the operating current and dump voltage above, a subdivision on a single coil basis (i.e. 16 coils) and two grades within each coil would result in a dump with a time constant below 1.5 s, compatible with a relatively high operating current density.

Finally, we consider the mass of such a gantry 100. Taking the winding geometry described above, the volume of the winding pack of a single coil is of the order of 0.06 m³, with an estimated mass of 400 kg/coil (with a typical 80/20 mix of conductor and insulation). As outlined above, each coil may be enclosed in a casing. With a casing thickness of 5 cm, a casing made of Al-alloy would have a weight of the order of 230 kg/coil. Finally, the coils must be wedged and supported against centering forces, as well as out-of-plane forces. In this example, this is done with an intercoil structure that forms the central bucking cylinder (as described above) and an outer belt. With an extent of the intercoil structure of the order of 1 m along the z-direction, the mass of an Al-alloy structure is estimated at 1.7 tons. The total mass of the gantry 100 is thus of the order of 12 tonnes, which is advantageously a major weight reduction with respect to the typical weight of a state-of-the art proton gantry, which may typically be well over 100 tonnes.

Use of More than One Toroidal Magnet

The above detailed description has been primarily in relation to a gantry comprising one (i.e. a single) toroidal magnet. However, the present invention may utilise a gantry comprising two or more toroidal magnets, as has been schematically illustrated in FIG. 1. We now discuss this concept in more detail with reference to FIG. 19.

FIG. 19 schematically illustrates an apparatus 1000 for charged particle therapy. Here the apparatus comprises a vector magnet 20 and a gantry 100 comprising two toroidal magnets 10a and 10b. Only one coil of each magnet has been shown for clarity. The toroidal magnets have a common primary axis, here aligned along the z axis, and are spaced along the primary axis by a distance D. A vector magnet 20 receives a beam of charged particles 35 from a particle accelerator extraction line and provides deflection of the beam dependent on momentum to charge ratio, as has been discussed above.

In the case of a gantry comprising a single toroidal magnet (e.g. as shown in and described with reference to FIG. 12), particle beams with larger p/q ratios are typically deflected through a larger angle by the vector magnet 20 in order that they enter the toroidal magnet at a larger radial distance from the primary axis than particles with smaller p/q. The geometry of the toroidal magnet is such that the beams with larger p/q entering at a larger radial distance travel further through the magnetic field in order that the beams are focused to a common point.

In the present two-magnet example shown in FIG. 19, the combined geometry of the magnets 10a and 10b is such that the vector magnet 20 is required to deflect beams of higher p/q through a smaller angle with respect to the primary axis than beams of smaller p/q. In the current example, two particles beams 30a and 30b are schematically illustrated, with beam 30a having a smaller momentum than beam 30b. The vector magnet is configured to deflect beam 30a through a larger angle than beam 30b such that beam 30a enters first toroidal magnet 10a at a larger radial distance from the primary axis than beam 30b.

The geometry of first toroidal magnet 10a is such that beam 30a entering the magnet at a larger radial location travels further through the magnetic field and is thus deflected through a larger angle than beam 30b that enters the first toroidal magnet 10a at a smaller radial location. Consequently, as the beams move through the gantry, beam 30b (having higher p/q ratio) enters the second toroidal magnet 10b at a larger radial location than beam 30a and travels further through the magnetic field of the second toroidal magnet 10b. As such the beams are focused to a common point on the primary P on the primary axis.

In this example, the coils of the second toroidal magnet 10b have substantially the same geometry as the magnet discussed above with reference to FIG. 7. The coils of the first toroidal magnet 10a have a geometry such that a leading edge 12a of a coil (i.e. proximal to the vector magnet) is orientated at an angle φ with respect to the primary axis that is smaller than the angle between the trailing edge 12b (i.e. distal to the vector magnet) of the toroidal magnet and the primary axis. In other words, a dimension of the coils along a direction substantially parallel with the primary axis substantially increases with radial distance from the primary axis. This means that particle beams entering the first toroidal magnet 10a at larger radial distance from the primary axis travel further within its magnetic field.

It will be appreciated that the examples of the toroidal magnet geometry discussed herein are examples only, and other geometries and relative positions of the one or more toroidal magnets and their relationship with the deflection provided by the bending device such that beams of different p/q are focused to a common point, are envisaged.

Vector Magnet

The vector magnet produces a bending power that bends the beam of charged particles (e.g. from a particle accelerator extraction line) through a deflection angle with respect to the primary axis. For proton beams having an energy between 70 and 250 MeV, typical deflection angles are in the range of approximately 10 to 20 degrees from the primary axis. Similar deflection angles are necessary for ion beams. Thus, the vector magnet can be seen to deliver a 170 to 350 mrad "kick" to the incident particle beams.

The vector magnet may also have scanning functionality, with a typical bending angle of 1 degree (17 mrad "kick").

Two preferred embodiments of a vector magnet that may be used in the present invention are described with reference to FIG. 20 which illustrates a rotating vector magnet, and FIG. 21 which illustrates a fixed vector magnet.

Figure 20A:
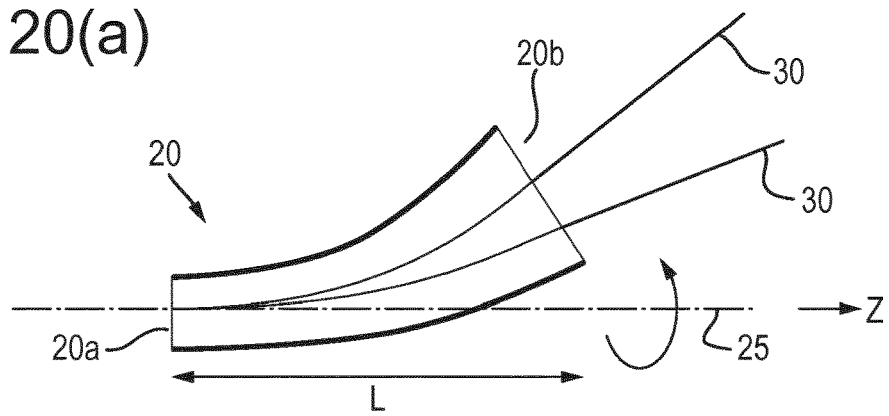
FIGS. 20(a) to 20(c) illustrate a first preferred example of a vector magnet that may be used in the present invention.
Figure 20B:
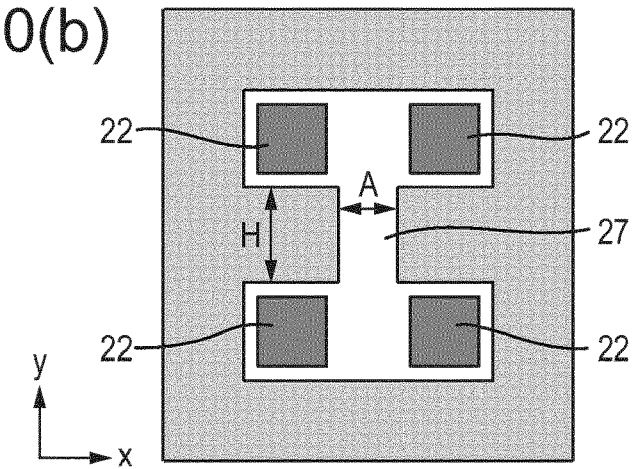
Figure 20C:
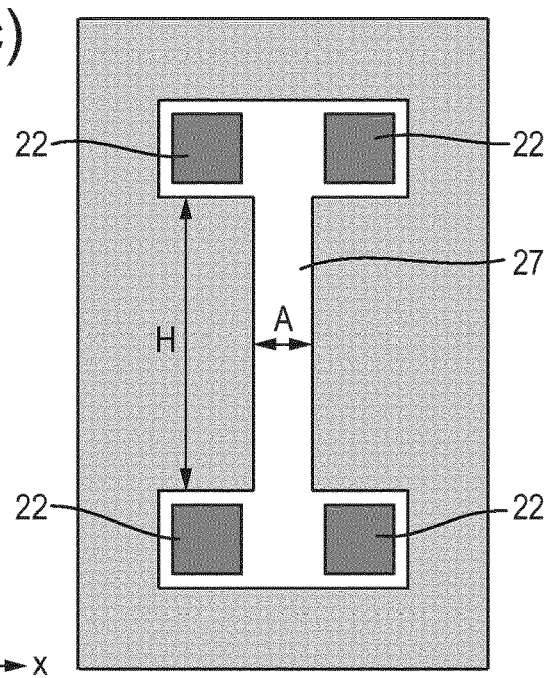

FIG. 20($a$) is a schematic side view of a rotating vector magnet 20 that rotates about rotation axis 25. A rotating vector magnet provides fast energy switching and relatively slow change of direction. Rotation axis 25 is typically coincident with the primary axis of the toroidal magnet. Particle beams (shown at 30) enter the vector magnet at beam entry point 20a, and exit at beam exit point 20b. A typical elongate length, L, of the vector magnet is in the range of 0.7-1.0 m, typically 0.8 m. This provides an integral magnetic field of 1 T (e.g. suitable for 250 MeV protons).

FIG. 20($b$) is a schematic cross section of the vector magnet 20 at beam entry point 20a. The vector magnet comprises a plurality of resistive magnets 22 that define an aperture 27 (illustrated by the non-shaded region) having a minimum width shown at A. In the case of a rotating vector magnet, the aperture A has a width of the order of a few centimetres. Preferred minimum dimensions A of the aperture are in the range of 3 cm to 5 cm.

At the beam entry point 20a, typical distances between resistive magnets 22 perpendicular to the primary axis (which may be referred to as a height, H, of the vector magnet) are in the range of 6 cm to 10 cm. The height of the vector magnet increases along its length, with a typical height of the vector magnet at its beam exit point 20b being 20 cm (see FIG. 20($c$)). The minimum dimension of the aperture, A, remains of substantially constant dimension along the length of the vector magnet.

Figure 21A:
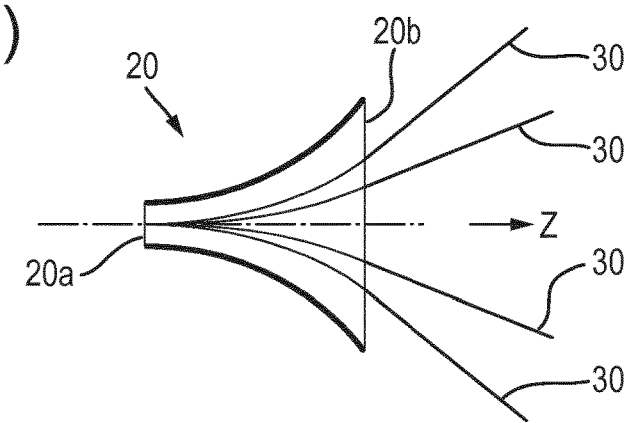
FIGS. 21(a) to 21(c) illustrate a second preferred example of a vector magnet that may be used in the present invention.
Figure 21B:
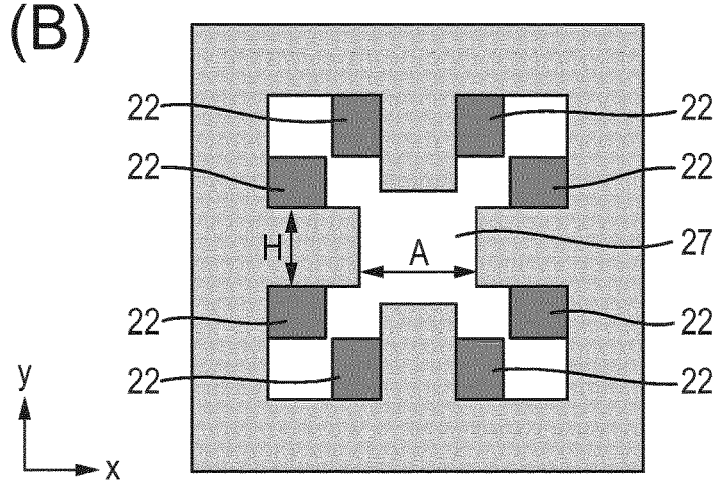
Figure 21C:
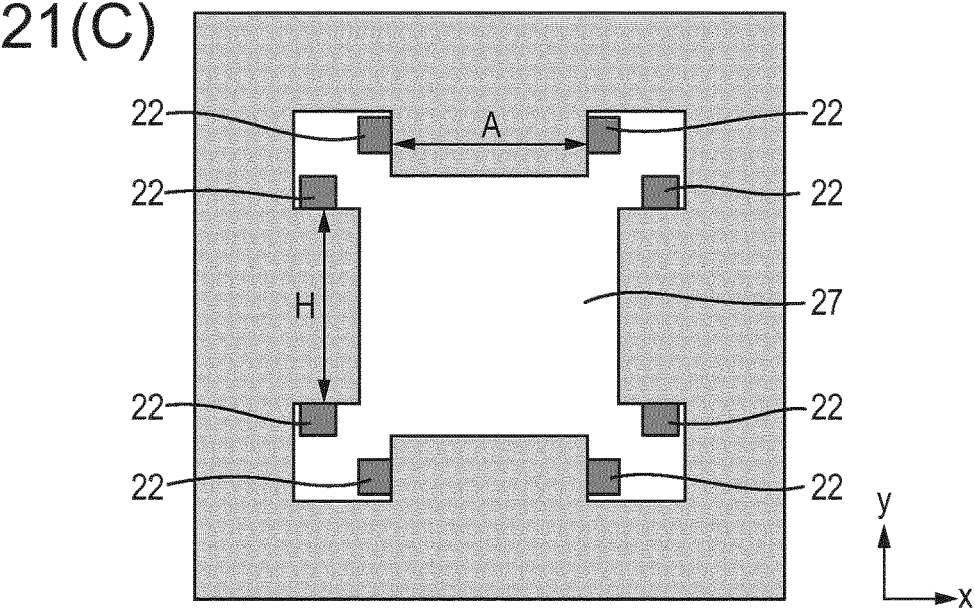

FIG. 21 ($a$) is a schematic side view of a fixed vector magnet, which is in the form of a combined two-plane kicker magnet formed using resistive magnets 22. Only one plane is shown in FIG. 21. Such a fixed vector magnet provides for both fast energy and direction switching. FIG. 21 ($b$) illustrates a cross-sectional view of the magnet at beam entry point 20a, with a typical aperture dimension A in the range of 3 cm to 5 cm. Typical values for H at the beam entry point 20a are in the range of 3 cm to 5 cm.

The cross sectional area and aperture size A of the vector magnet 20 increase along its length to accommodate the range of exit angles of the particle beams 30. In this example, the cross sectional geometry of the vector magnet remains substantially square. In this example, at the beam exit point (FIG. 21 ($c$)), the aperture has a gap A of approximate dimension 20 cm, with typical dimensions for H at the beam exit point 20b are also approximately 20 cm.

The invention claimed is:

1. A gantry for focusing beams of charged particles having differing momentum to charge ratios to a substantially common point, comprising:

at least one toroidal magnet having a central bore, a primary axis of the at least one toroidal magnet extending along the central bore, the at least one toroidal magnet configured to receive beams of charged particles at different radial locations dependent on a momentum to charge ratio of each beam;

wherein the at least one toroidal magnet comprises a plurality of discrete, substantially planar coils spaced apart and extending radially from the primary axis and configured to produce a magnetic field such that, in use, a first beam of charged particles having a component of motion along the primary axis and entering the at least one toroidal magnet at a first radial location, is directed towards a first point on the primary axis, and;

a second beam of charged particles having a different momentum to charge ratio to the first beam, and having a component of motion along the primary axis and entering the at least one toroidal magnet at a second radial location, is directed towards said first point on the primary axis, and wherein:

the magnetic field is periodically symmetric about the primary axis, and the at least one toroidal magnet is substantially stationary in use.

2. The gantry of claim 1, wherein the magnetic field is substantially static in use.

3. The gantry of claim 1, wherein the plurality of planar coils are superconducting coils.

4. The gantry of claim 1, wherein the plurality of planar coils is positioned in a periodic manner about the primary axis.

5. The gantry of claim 1, wherein the plurality of planar coils has a non-symmetrical geometry.

6. The gantry of claim 1, wherein the plurality of planar coils is elongate in a direction substantially parallel to the primary axis, and has a geometry such that a radial dimension of the plurality of planar coils varies along an elongate length.

7. The gantry of claim 6, wherein the plurality of planar coils has a minimum radial dimension at a first end of the at least one toroidal magnet and a maximum radial dimension at a second opposing end of the at least one toroidal magnet.

8. The gantry of claim 7, wherein the minimum radial dimension is at an end of the at least one toroidal magnet where the beams of charged particles enter the at least one toroidal magnet.

9. The gantry of claim 7, wherein a radially outer portion of each planar coil is arranged substantially parallel with the primary axis, and a radially inner portion of each planar coil extends between a radial maximum portion of each planar coil having the maximum radial dimension and a radial minimum portion having the minimum radial dimension such that the radial dimension of each planar coil varies along its elongate length.

10. The gantry of claim 1, wherein the plurality of planar coils is configured to provide geometric and/or current grading.

11. The gantry of claim 1, wherein the plurality of planar coils is geometrically graded in a radial direction.

12. The gantry of claim 1, wherein at least one planar coil comprises ferromagnetic material.

13. The gantry of claim 1, further comprising a support structure adapted to support the plurality of planar coils, wherein the support structure is configured to allow passage of each beam of charged particles through the gantry in use.

14. The gantry of claim 13, wherein the support structure comprises at least one aperture at a radially inner part thereof such that a beam of charged particles can pass into the central bore.

15. The gantry of claim 1, wherein in use beams of charged particles are received at the at least one toroidal magnet at a non-zero angle with respect to the primary axis.

16. The gantry of claim 1, wherein the magnetic field is further configured such that beams of different momentum to charge ratio are directed towards a substantially common point on the primary axis along a trajectory that is substantially 90 degrees to the primary axis.

17. An apparatus for focusing charged particles, comprising:

a bending device configured to receive beams of charged particles, and;

a gantry according to claim 1, wherein the bending device is configured to direct beams of charged particles towards the gantry dependent on the momentum to charge ratios of the beams such that beams of charged particles having different momentum to charge ratios are directed towards a common point on the primary axis of the gantry.

18. The apparatus of claim 17, wherein the bending device is configured to direct the beams of charged particles towards the gantry at a non-zero angle with respect to the primary axis.

19. The apparatus of claim 17, wherein the bending device comprises a vector magnet.

20. The apparatus of claim 17, wherein the apparatus is for use in charged particle therapy, and wherein, in use, a subject is positioned within the central bore of the at least one toroidal magnet.

21. The gantry of claim 1, wherein the gantry is for use in charged particle therapy, and wherein, in use, a subject is positioned within the central bore of the at least one toroidal magnet.

* * * * *